(12) United States Patent
Oi et al.

(10) Patent No.: US 8,474,448 B2
(45) Date of Patent: Jul. 2, 2013

(54) METERED DOSE INHALER

(75) Inventors: Yoshihiro Oi, Osaka (JP); Shintaro Adachi, Naka-gun (JP); Takaaki Nakao, Naka-gun (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 463 days.

(21) Appl. No.: 12/680,123

(22) PCT Filed: Sep. 26, 2008

(86) PCT No.: PCT/JP2008/067562
§ 371 (c)(1),
(2), (4) Date: Mar. 25, 2010

(87) PCT Pub. No.: WO2009/041662
PCT Pub. Date: Apr. 2, 2009

(65) Prior Publication Data
US 2010/0192946 A1    Aug. 5, 2010

(30) Foreign Application Priority Data

Sep. 26, 2007  (JP) .................................. 2007-249886
Mar. 6, 2008   (JP) .................................. 2008-056759

(51) Int. Cl.
*A61M 11/00* (2006.01)
(52) U.S. Cl.
USPC ................................................... 128/200.23
(58) Field of Classification Search
USPC ............. 128/200.23, 200.21, 200.15, 200.14, 128/203.21, 205.23, 203.12, 203.15, 200.24
See application file for complete search history.

(56) References Cited

U.S. PATENT DOCUMENTS

| 6,446,627 | B1 | 9/2002 | Bowman et al. | |
|---|---|---|---|---|
| 6,659,307 | B1 | 12/2003 | Stradella | |
| 7,575,003 | B2 * | 8/2009 | Rasmussen et al. | 128/200.23 |
| 7,780,038 | B2 * | 8/2010 | Ingram et al. | 222/36 |
| 8,006,695 | B2 * | 8/2011 | Lulla et al. | 128/203.21 |
| 2007/0084467 | A1 * | 4/2007 | Scarrott et al. | 128/205.23 |
| 2007/0251950 | A1 | 11/2007 | Bacon | |
| 2008/0029085 | A1 * | 2/2008 | Lawrence et al. | 128/200.14 |
| 2008/0035144 | A1 | 2/2008 | Bowman et al. | |
| 2008/0105256 | A1 * | 5/2008 | Lulla et al. | 128/203.21 |

FOREIGN PATENT DOCUMENTS

| JP | 2003-512265 A | 4/2003 |
|---|---|---|
| JP | 2007-513666 A | 5/2007 |
| WO | 2006-110080 A1 | 10/2006 |

* cited by examiner

*Primary Examiner* — Melanie Hand
*Assistant Examiner* — Mark Wardas
(74) *Attorney, Agent, or Firm* — Sughrue Mion, PLLC

(57) ABSTRACT

The present invention provides an improved metered dose inhaler utilizing the property of the aerosol canister. The metered dose inhaler includes: a housing body (2); an aerosol canister (3) including a canister body (3a), a valve stem (3b), and a spring urging the valve stem, wherein the valve stem (3b) is held at a fixed position inside the housing body (2), and wherein the canister body (3a) is supported inside the housing body (2) to be depressible against a spring force of the spring; a dose counter (10) including display members (12) and (13) rotatably supported inside the housing body (2), and a control lever (14) swingably supported inside the housing body (2) to rotate the display member (13); and a control cap (20) including a junction member rotatably joined to the control lever (14), and a cap portion (20b) which sheaths the canister body (3a) from a bottom side of the canister body (3a), wherein the control cap (20) causes the control lever (14) to swing.

7 Claims, 33 Drawing Sheets

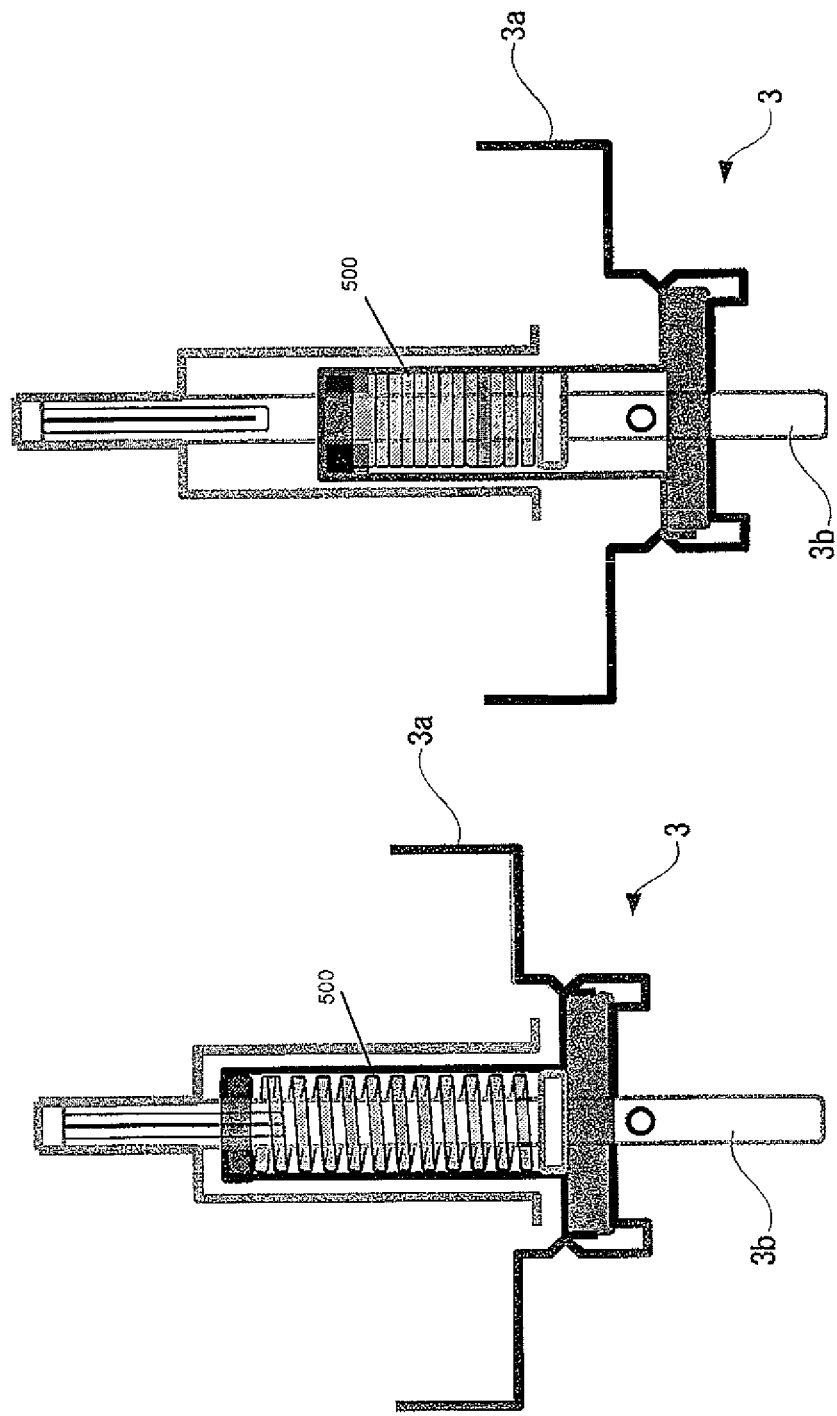

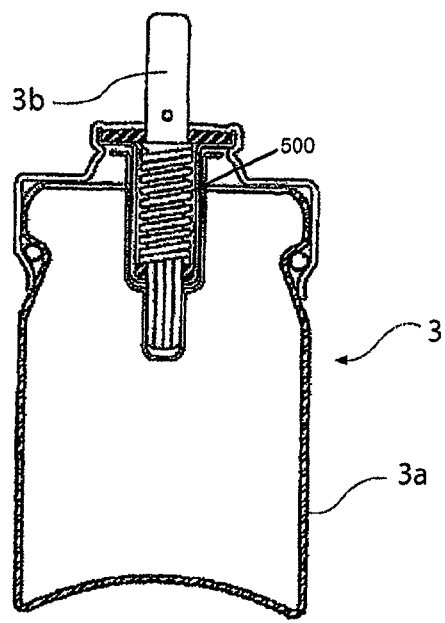
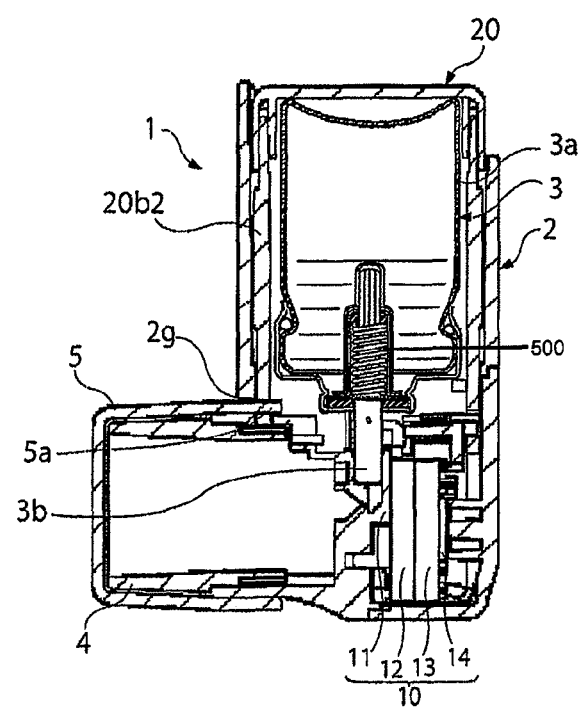
FIG. 52
FIG. 53

METERED DOSE INHALER

TECHNICAL FIELD

The present invention relates to metered dose inhalers.

BACKGROUND ART

As known conventionally, a metered inhaler is a device for the treatment of asthma. The dry powder inhaler (DPI) and the metered dose inhaler (MDI) are known examples of such inhalers. The metered dose inhaler is also known as a pressurized metered dose inhaler (pMDI).

Generally, the metered dose inhaler includes an aerosol canister containing medication. The aerosol canister generally includes a canister body, a valve stem extending from the canister body, and a spring installed in the canister body. The valve stem is urged to close by the spring, and releases an aerosol when depressed against the force of the spring. The valve stem is commonly held by the aerosol canister attached to the metered dose inhaler. A patient manually depresses the bottom of the canister body to push the valve stem into the canister body. The medicament-containing aerosol released from the valve stem travels through a channel inside the housing body to be ejected out of the mouthpiece attached to the housing body.

Metered dose inhalers provided with a dose counter for displaying the number of doses are widely known. The dose counter is either electronic (for example, reference 1) or mechanical (for example, References 2 and 3). In terms of cost, the mechanical dose counter is more advantageous than the expensive, electronic dose counter. The mechanical dose counter is also advantageous to provide disposable metered dose inhalers.

A known mechanical dose counter includes an indicator panel carrying marks to indicate the number of doses and which is rotatably supported, and a control lever for rotating the indicator panel. The control lever is urged to return to the initial position by an elastic means such as a spring. When the canister body of the aerosol canister is manually depressed, the downward force on the aerosol canister moves the control lever downward against the urging force of the spring of the control lever. The control lever is sprung back to the original position on release of the downward force on the aerosol canister. The control lever engages the indicator panel and rotates it by a predetermined angle while being depressed or returning to the original position. That is, in one stroke of reciprocal movement, the control lever rotates the indicator panel to increment the display by one.

Reference 1: JP-T-2007-513666
Reference 2: JP-T-2003-512265
Reference 3: U.S. Pat. No. 6,446,627

DISCLOSE OF INVENTION

Problem to be Solved by the Present Invention

However, further improvement of the metered dose inhalers utilizing the property of the aerosol canister as the mechanical dose counter has been expected.

The present invention provides an improved metered dose inhaler utilizing the property of the aerosol canister.

Means for Solving the Problem

According to a first aspect of the invention, there is provided a metered dose inhaler including:

a housing body;

an aerosol canister including a canister body, a valve stem, and a spring urging the valve stem, wherein the valve stem is held at a fixed position inside the housing body, and wherein the canister body is supported inside the housing body to be depressible against a spring force of the spring;

a dose counter including at least one display member rotatably supported inside the housing body, and a control lever swingably supported inside the housing body to rotate the display member; and a control cap including at least one junction member rotatably joined to the control lever, and a cap portion which sheaths the canister body from a bottom side of the canister body, wherein the control cap causes the control lever to swing and return, by utilizing an elastic force of the spring of the aerosol canister.

With this configuration, the structure of the metered dose inhaler can be simple since the spring force of the aerosol canister is utilized.

The metered dose inhaler may further comprise a removing means for removing at least cap portion of the control cap from the control lever. For example, the removing member may include a frangible portion between the junction member and the cap portion to sever the cap portion from the junction member. The frangible portion may be a thin-walled portion. Alternatively, the removing means may include the junction member which can be bent to disconnect the connection between the junction member and the control lever.

The metered dose inhaler may further include a mouthpiece attached to the housing body, and a mouthpiece cap covering the mouthpiece, wherein the mouthpiece cap includes a protrusion to operate the disconnecting means. The housing body may include the disconnecting means having a thin film portion which is punctured by the protrusion. Further, the metered dose inhaler may be adapted to so that the housing body includes a through-hole through which the protrusion penetrates into the housing body when the mouthpiece cap is attached to the mouthpiece, and that the protrusion penetrates into the housing body through the through-hole to limit a depression displacement of the aerosol canister.

The metered dose inhaler may be adapted so that the dose counter includes an auxiliary spring to return the control lever. The spring force of the auxiliary spring is not limited. For example, the auxiliary spring has a spring force insufficient to return the control lever by itself, but strong enough to cause a return of the control lever with the aid of the spring force of the spring of the aerosol canister. Such a spring may be mounted in the below-mentioned second invention of the metered dose inhaler.

The metered dose inhaler may be adapted to further include:

a mouthpiece attached to the housing body;
a mouthpiece cap to cover the mouthpiece; and
a lock mechanism to limit a depression displacement of the aerosol canister when the mouthpiece cap is attached to the mouthpiece, wherein the mouthpiece cap includes a protrusion, capable of penetrating through a through-hole of the housing body when the mouthpiece cap is attached to the mouthpiece, and wherein the lock mechanism includes:
a slanted guide face formed on a lower edge of the cap portion, along a circumference of the cap portion; and
a lock member including a slanted face, movable along the slanted guide face by being slidably guided by the slanted guide face, and a lock portion, interlocking with the protrusion to prevent movement of the slanted face, wherein the lock member limits depression displacement of the control cap by supporting the slanted guide face on the slanted face at a position where movement of the slanted face is prevented by the lock portion, and wherein the lock member releases the lock portion from the protrusion to allow movement of the slanted face and thereby depression displacement of the control cap.

According to a second aspect of the invention, there is provided a metered dose inhaler including:

an aerosol canister including a canister body, a valve stem extending from the canister body, and a spring urging the valve stem, the valve stem being depressed to release contents of the aerosol canister;

a housing body, provided with a holder holding the valve stem of the aerosol canister, to house the aerosol canister;

a dose counter including at least one display member rotatably supported inside the housing body, and a control lever supported inside the housing body to rotate the display member; and a control cap including at least one junction member capable of engaging the control lever, and a cap portion covering the canister body from an opposite side of the valve stem, the aerosol canister being supported in the housing body to enable the canister body to be depressed against an urging force of the spring, the canister body of the aerosol canister including an engaging part to engage the control lever, the control lever being movable between a first position and a second position, the first position being a predetermined position between a tip of the valve stem and the engaging part, and the second position being a depressed position of the control lever engaging the engaging part of the canister body, the control cap co-operating with the canister body to be depressed from an initial position, and co-operating with the canister body to return to the initial position from a depressed position by the spring of the aerosol canister, the engaging part of the canister body engaging the control lever to move the control lever from the first position to the second position, when the canister body is depressed with the control cap, the junction member of the control cap moving the control lever from the second position to the first position when returning to the initial position, and the control lever rotating the display member when moving from the first position to the second position, or when returning to the first position from the second position.

With this configuration, the structure of the metered dose inhaler can be simple since the spring force of the aerosol canister is utilized. The shape of the control lever is not limited. For example, the control lever may be provided with the engaging portion to engage with the aerosol canister. The aerosol canister does not always contact the control lever directly. The aerosol canister may indirectly contact the control lever via other member.

Often, there is variation in the length of the valve stem due to manufacturing error of the aerosol canister. For example, an aerosol canister with a longer valve stem tends to require a longer depression distance for the valve stem, from the point of depression to the release of the contents, compared with an aerosol canister with a shorter valve stem requiring a shorter depression distance.

In the present invention, the control lever is disposed at a predetermined position between the engaging part of the canister body and the tip of the valve stem. This is advantageous in the following respect. For example, with this configuration, a longer valve stem would require a longer distance for the canister body to engage the control lever after depression, whereas a shorter valve stem requires a shorter depression distance to engage the control lever. By taking advantage of the relationship between the length of the valve stem and the depression distance required for ejection, the depression distance for ejecting the contents after the engaging part of the canister body has engaged the control lever can be made substantially the same regardless of the valve stem length. That is, the time from the ejection of the contents to the update of the dose counter operated by the control lever can be made substantially the same even when there is variation in the length of the valve stem, so that a patient will not notice a time lag due to a difference in length of the valve stem.

The metered dose inhaler may be adapted so that the control lever engages the display member and rotates the display member when moving from the second position to the first position.

The metered dose inhaler may be adapted so that the control lever includes a stopper, which locks the display member at the first position, and unlocks the display member at the second position. With this configuration, the rotation of the display member is locked when the control lever is at the initial, first position, preventing accidental rotation of the display member and malfunction of the dose counter.

The control lever can have various configurations, for example as follows. The control lever may be configured so that it includes a protrusion capable of engaging the junction member, and is swingably supported between the first position and the second position, wherein the control lever swings from the first position to the second position in response to depression of the control cap, and wherein the junction member and the protrusion move together without engaging each other following the swing of the control lever in response to depression of the control cap, and wherein the junction member moves the control lever from the second position to the first position by being engaged by the protrusion, when moved with the control cap returning to the initial position.

Further, the metered dose inhaler may be adapted so that the canister body includes a step on a surface having the valve stem, and wherein the step comprises the engaging part. The engaging member is not limited to the step, as long as it can push the control lever by engaging the control lever.

Further, the metered dose inhaler may be adapted to further include: a mouthpiece detachably attached to the housing body, wherein contents of the aerosol canister are ejected out of the housing body through the mouthpiece. By the provision of the mouthpiece, the contents ejected from the aerosol canister can be directly sent into the mouth.

It is easy to wash the mouthpiece because it is detachably mounted.

Further, the metered dose inhaler may be adapted so that the control cap further includes supporting means to support the canister body from a side of the valve stem. This prevents advancement of the counter by the movement of the canister body during assembly of the inhaler. Further, this also prevents the canister body only from moving by the force of impact. As a result, the advancement of the counter or the ejection from the canister body can be prevented.

Advantageous Effect

With a metered dose inhaler according to the present invention, the compressive force of the aerosol canister required for inhaling can be reduced.

BEST MODE FOR CARRYING OUT THE INVENTION

The following will describe embodiments of a metered dose inhaler according to the present invention.

First Embodiment

A First Embodiment of a metered dose inhaler according to the present invention is described below with reference to FIG. 1 through FIG. 17.

As shown in FIG. 1, a metered dose inhaler 1 includes a housing body 2, and an aerosol canister 3 housed in the housing body 2. As shown in FIG. 2, a mouth piece 4 is attached to the housing body 2, and a mouthpiece cap 5 is detachably provided for the mouthpiece 4.

The aerosol canister 3, as shown in FIGS. 3 and 4, includes a substantially cylindrical, canister body 3a, and a valve stem 3b protruding from an end of the canister body 3a. By a coil spring 500 (see FIG. 50) it contains, the valve stem 3b is urged in the direction of protrusion so that the valve remains closed. FIGS. 52 and 53 illustrate an interior cross-section of FIGS. 3 and 4.

The housing body 2 includes a cylindrical portion 2a providing an accommodation for the aerosol canister, as shown in FIG. 5. The aerosol canister 3, as shown in FIG. 3, is inserted into the housing body 2 upside down, with the valve stem 3b facing downward. Referring to FIG. 5, the housing body 2 includes therein a holder 2b for holding the valve stem 3b. The holder 2b includes a fitting hole 2b1 formed to fit the valve stem 3b airtight. The housing body 2 further includes an orifice 2c, in communication with the fitting hole 2b1, and a funnel portion 2d in communication with the orifice 2c. Through the funnel portion 2d, the aerosol released from the valve stem 3b is guided into the mouthpiece 4.

Pressing down the canister body 3a of the aerosol canister 3 against the elastic force of the internal coil spring 500 pushes the valve stem 3b into the aerosol canister 3 (see FIG. 51), opening the valve of the valve stem 3b and thereby permitting the medicament to enter the valve stem 3b, which then releases the aerosol into the mouthpiece 4 through the orifice 2c and the funnel portion 2d.

Referring to FIGS. 3 and 4, a dose counter 10 is provided inside the housing body 2. The dose counter 10 includes a support member 11 fixed to an inner surface of the housing body 2, a pair of display members 12 and 13 rotatably supported by the support member 11, and a control lever 14 used to rotate the display members 12 and 13.

For example, the tens-place numbers 0 to 10 are printed at regular intervals on a circumferential side surface of the display member 12. Similarly, the ones-place numbers 0 to 9 are shown on a circumferential side surface of the display member 13. The dose counter 10 is therefore able to display the numbers 0 to 109. On a side surface of the housing body 2, as shown in FIGS. 1 and 2, a window 2w is formed through which the numbers (not shown) on the display members 12 and 13 are viewed. As shown by the exploded perspective views of FIGS. 6 and 7, the display members 12 and 13 are annular rings having shaft holes 12a and 13a, respectively.

FIG. 8 is an enlarged, partial perspective view of FIG. 6. FIG. 9 is an enlarged, partial perspective view of FIG. 7. Referring to FIG. 8, the display member 12 includes a plurality of circumferential, locking grooves 12b formed on its side opposite from the display member 13. The support member 11, as shown in FIG. 9, includes detent pawls 11a, 11a interlocking with the locking grooves 12b. The detent pawls 11a, 11a and the locking grooves 12b are formed such that the detent pawls 11a, 11a prevent rotation of the display member 12 in the direction of arrow A, but, by being elastic, permit rotation of the display member 12 in the direction of arrow B when a predetermined torque is applied to the display member 12 in this direction.

FIG. 10 is an enlarged, partial perspective view of FIG. 7. FIG. 11 is an enlarged, partial perspective view of FIG. 6. In FIGS. 10 and 11, the display member 12, disposed between the support member 11 and the display member 13, is omitted for convenience of explanation.

On the inner circumferential surface of the shaft hole 13a of the display member 13, a plurality of equiangular, locking grooves 13b are formed that extends along the axial direction, as shown in FIG. 10. The support member 11 includes detent pawls 11b, 11b interlocking with the locking grooves 13b. The locking grooves 13b and the detent pawls 11b, 11b are formed such that the detent pawls 11b, 11b prevent rotation of the display member 13 in the direction of arrow A, but, by being elastic, permit rotation of the display member 13 in the direction of arrow B when a predetermined torque is applied to the display member 13 in this direction.

The display member 13 further includes a plurality of circumferential, locking grooves 13c formed on its side opposite from the display member 12, as shown in FIG. 10. The control lever 14 is swingably supported by a shaft 11c formed on the support member 11. The tip of the control lever 14 is a locking pawl 14a interlocking with the locking grooves 13c (FIG. 11). When swung in the direction of arrow B1, the control lever 14 swings with the locking pawl 14a interlocked with the locking grooves 13c, exerting a predetermined torque to the display member 13 and rotating it in the direction of arrow B. When the control lever 14 is swung in the direction of arrow A1, the locking pawl 14a slides on a slanted face 13d of the display member 13 (FIG. 10), because the rotation of the display member 13 in the direction of arrow A is prevented by the detent pawls 11b, 11b. In one stroke of reciprocal movement of the control lever 14, the display member 13 is rotated 36°. Accordingly, the number of the dose counter shown via the window 2w is incremented.

As shown in FIG. 9, the display member 12 includes a plurality of circumferential, locking grooves 12c on its side in contact with the display member 13. Referring to FIG. 11, the display member 13 includes a locking pawl 13e interlockable with the locking grooves 12c. The locking pawl 13e, as shown in FIG. 10, has a protrusion 13f on the side opposite from the display member 12. The protrusion 13f is formed to slide up along a raised portion 2k formed on an inner side of a part 2y of the housing body 2, as shown in FIG. 12, which is a partial magnified view of FIG. 6. When the display member 13 rotates to change the display from "9" to "0", the protrusion 13f of the locking pawl 13e slides up along the raised guide 2k to push the locking pawl 13e toward the locking grooves 12c, causing the locking pawl 13e to interlock with one of the locking grooves 12c and rotate the display member 12 with the display member 13, thereby advancing the tens-place number on the display member 12. When the protrusion 13f is not up on the raised portion 2k, the locking pawl 13e is not interlocked with the locking grooves 12c.

Referring to the enlarged, partial perspective view of FIG. 13, a control cap 20 includes a junction member 20a rotatably joined to the control lever 14, and a cap portion 20b which sheaths the canister body 3a from a bottom side of the canister body 3a.

The cap portion 20b may include a base plate 20b1, which can be brought into contact with the bottom of the aerosol canister, and a shell 20b2, surrounding the circumferential wall of the aerosol canister. The shell 20b2 includes cam followers 20c. The cam followers 20c engage cam grooves 2e (FIG. 1) formed on the inner circumferential surface of the housing body 2. The cam grooves 2e extend along the axial direction of the cylindrical portion 2a (FIG. 5) of the housing body 2 to guide the reciprocal movement of the control cap 20.

It should be noted here that the cap portion 20b shown in the figures is a two-component member including an upper part (base plate 20b1) and a lower part (shell 20b2 and junction member 20a), which are coupled together as shown in FIGS. 6 and 7. This is for ease of manufacture and the cap portion 20b may be a single-component member.

As shown in FIG. 13, the junction member 20a includes a hooked portion formed at an end of a projection 20d extending out from the lower edge of the shell 20b2 of the cap portion 20b. Referring to FIGS. 10 and 11, the control lever 14 includes a link pin 14c between the locking pawl 14a and the hole 14b for receiving the shaft 11c. As shown in FIGS. 14 and 15, the control lever 14 is rotatably joined to the junction member 20a by the engagement of the hooked portion of the junction member 20a with the link pin 14c. Accordingly, the vertical reciprocal movement of the control cap 20 causes the control lever 14 to swing back and forth and rotate the display member 12.

Note that the junction member 20a is not limited to the configuration shown in the figures as long as it is rotatably joined to the control lever 14. For example, the junction member may be a link pin, and the control lever may include a pinhole fitted to the link pin.

As shown in FIG. 13, another junction member 20a' is formed in addition to the junction member 20a. The junction member 20a' is provided to join to a control lever 14' (see FIGS. 16 and 17) having a different swing angle. The control lever 14' includes a link pin 14c' and a hole 14b', which are more distant apart from each other compared with the control lever 14. Thus, provided that the reciprocating stroke of the control cap 20 is the same, the control lever 14' swings in a smaller angle than the control lever 14. For example, it is possible to make appropriate use of the control lever 14', having a smaller swing angle, and the control lever 14, having a larger swing angle, for adults and children, respectively, by assembling these members to join to either the junction member 20a' or the junction member 20a.

The control lever 14, as shown in FIGS. 10 and 11, includes a stopper 14s, which prevents the display members 12 and 13 from rotating by accident when the control lever 14 is not swinging. The stopper 14s includes protrusions 14s1 engaging in recesses 12x (see FIG. 9), 13x formed equiangularly on the circumferential surface of the display member 12, 13.

Referring to FIG. 13, the control cap 20 includes a frangible portion 20e used to sever the cap portion 20b and the junction member 20a from each other. The frangible portion 20e may be a thin-walled portion formed by a transverse groove formed along the width of the projection 20d, as shown in the figure. The frangible portion 20e is not particularly limited as long as it is strong enough to avoid fracture during normal operation of the control lever 14. For example, the frangible portion 20e may be formed by reducing width, instead of thickness as shown in the figure.

The mouthpiece cap 5, as shown in FIG. 2, may have a protrusion 5a used to break the frangible portion 20e. The frangible portion 20e may be broken by other means or methods, though the use of the protrusion 5a is preferred. Alternatively, the junction member 20a may be provided with a hinge. By this configuration, when the protrusion 5a is inwardly pushed, the connection between the junction member and the control lever can be disconnected by bending the junction member 20a inwardly. For example, the housing body 2, assembled from the two parts 2x and 2y as shown in FIGS. 6 and 7, may be structured to include a detachable part 2y, so that the frangible portion 20e can be manually broken by a user with a finger nail after detaching the part 2y.

As shown in FIGS. 3, 4, and 7, the housing body 2 includes a thin film portion 2f which can be punctured by the protrusion 5a. The protrusion 5a punctures the thin film portion 2f and hits a portion slightly below the frangible portion 20e of the control cap 20 to cause a fracture in the frangible portion 20e. The protrusion 5a preferably has an acuate end so that it can easily puncture the thin film portion 2f. Instead of the thin film portion 2f, a perforation may be provided.

The housing body 2 includes a through-hole 2g (FIG. 5) through which the protrusion 5a penetrates into the housing body 2 when the mouthpiece cap 5 is attached to the mouthpiece 4. As shown in FIG. 3, the protrusion 5a protrudes into the housing body 2 through the through-hole 2g, and abuts on a tongue 20f (FIG. 6) provided on the edge of the shell 20b2 of the control cap 20. This prevents depression of the control cap 20 and the canister body 3a of the aerosol canister 3 to prevent malfunction. That is, with the mouthpiece cap 5 attached to the mouthpiece 4, the aerosol canister 3 cannot be depressed. Note that, though not shown, the protrusion 5a may be adapted to directly abut on the edge of the aerosol canister 3 to limit the depression displacement of the aerosol canister 3.

Actuation of the metered dose inhaler requires removal of the mouthpiece cap 5 from the mouthpiece 4. The following deals with the operation of the metered dose inhaler, with reference to FIGS. 14 and 15.

FIG. 14 is a partial, cutaway perspective view, before the canister body 3a is depressed inward of the housing 2.

In the state shown in FIG. 14, the stopper 14s is in engagement with the display member 12, 13 to prevent rotation and thus malfunction of the display member 12, 13. For example, an attempt to rotate the display member 12, 13 by accessing it through the window 2w of the housing 2 will fail by the stopper 14s.

FIG. 15 is a partial, cutaway perspective view showing a state in which the canister body 3a has been depressed into the housing 2.

With the mouthpiece cap 5 removed, the canister body 3a of the aerosol canister 3, via the cap portion 20b, is manually depressed by a user into the housing 2 against the internal coil spring 500 (see change from FIG. 50 to FIG. 51). This causes the control lever 14, joined to the junction member 20a, to swing downward, from the position shown in FIG. 14 to the lower position shown in FIG. 15. At the lower position, the locking pawl 14a of the control lever 14 interlocks with one of the locking grooves 13c of the display member 13 (see also FIG. 10).

When the canister body 3a of the aerosol canister 3 is depressed into the housing body 2, the valve stem 3b is pushed into the canister body 3a in reaction, then the metered medicament-containing aerosol is released from the valve stem 3b. Out of the valve stem 3b, the medicament-containing aerosol is released outside through the orifice 2c, the funnel portion 2d, and the mouthpiece 4 (see also FIG. 5).

After the medicament-containing aerosol is released, the compressive force exerted on the canister body 3a via the cap portion 20b is released. In response, the internal coil spring 500 of the aerosol canister 3 pushes back the control cap 20 with the canister body 3a. With the control cap 20 pushed back, the control lever 14, joined to the control cap 20, swings back to the original position shown in FIG. 14, from the lower position shown in FIG. 15. When the control lever 14 returns to the original position, the locking pawl 14$a$ interlocking with one of the locking grooves 13$c$ causes the display member 13 to rotate by a predetermined angle. This predetermined angle of rotation is the angle required to cause the display of the display member 13 to increment one. Note that, with the canister body 3$a$ back to original position, the valve stem 3$b$ returns to the original position and the medicament is filled for the next injection.

As described above, in the metered dose inhaler 1 of the First Embodiment, the control lever 14 is sprung back by the internal coil spring of the aerosol canister 3. Thus, the structure of the metered dose inhaler 1 can be simple.

Further, the metered dose inhaler 1 of the First Embodiment is made up of ten components excluding the aerosol canister 3. All of these components, except for the aerosol canister 3, can be formed by resin molding.

When the medicament in the aerosol canister 3 is used up in the metered dose inhaler 1, the frangible portion 20$e$ of the control cap 20 is broken by the protrusion 5$a$ to sever the cap portion 20$b$ from the junction member 20$a$. Because the cap portion 20$b$ simply caps the aerosol canister 3 and does not engage it, the cap portion 20$b$ can be readily drawn out from the housing body 2 after the cap portion 20$b$ is severed from the junction member 20$a$. Alternatively, when the junction member 20$a$ is bent around the frangible portion 20$e$ as fulcrum point so that the connection between the control lever 14 and the junction member 20$a$ is cut, the cap portion 20$b$ is readily removed from the housing body 2. Once the cap portion 20$b$ is drawn out, a user can easily take out the aerosol canister 3 because the valve stem 3$b$ is simply inserted into the holder 2$b$. This enables the aerosol canister 3, made of metal, to be easily separated for disposal from the other ten components formed of resin molded articles.

Second Embodiment

The following will describe a Second Embodiment of a metered dose inhaler according to the present invention, with reference to FIG. 18 through FIG. 28. The Second Example is a modification of the First Embodiment. As such, the descriptions below mainly deal with the changes made, and no further explanation will be made to those elements already described in the First Embodiment. Further, for ease of understanding, FIG. 18 through FIG. 28 only show relevant portions, and like elements in the First and Second Embodiments are given the same reference numerals.

As shown in FIGS. 18 and 19, a dose counter 100 of the Second Embodiment includes an auxiliary spring 101 used to return the control lever to initial position. The spring force of the auxiliary spring 101 itself is not sufficient to return the control lever 140, but is strong enough to cause a return of the control lever 140 with the aid of the spring force of the spring 500 of the aerosol canister.

Since the aerosol canister 3 is prone to manufacturing error, the auxiliary spring 101 is provided to complement the dimensional variations of the aerosol canister 3, or the variations in the spring force of the internal spring of the aerosol canister 3. As shown in the figures, the auxiliary spring 101 is a torsion spring, mounted on a shaft 110$c$ of a support member 110 to urge the control lever 140 toward the initial position.

For example, there are cases where the valve stem 3$b$ (see FIG. 20) or the vertical length of the canister body of the aerosol canister 3 is shorter than the designed dimension, or the spring force of the internal spring of the aerosol canister is smaller than expected. In these cases, the distance of depression of the valve stem 3$b$ releasing the aerosol will be smaller than intended. There accordingly will be a smaller compressive deformation in the internal spring urging the valve stem 3$b$. In this case, the return force of the spring urging the valve stem 3$b$ may become smaller than intended, too small to return the control lever 140. When returning, the control lever 140 interlocks with one of the locking grooves 13$c$ of the display member 13 to rotate the display member 13. Here, the force to rotate the display member 12, 13 needs to be strong enough to cause elastic deformation of the detent pawls 11$a$ (see FIG. 9), the detent pawls 11$b$ (see FIG. 10), or the protrusion 13$f$ (see FIG. 10). The control lever 140 cannot return when the return force of the spring urging the valve stem 3$b$ is not sufficient to cause elastic deformation of the detent pawls 11$a$ or the detent pawls 11$b$.

The auxiliary spring 101 assists the spring of the aerosol canister when there is variation in the aerosol canister 3 due to design error, ensuring a return of the control lever 140. In other words, the auxiliary spring 101 is provided to prevent malfunction due to manufacturing error of the aerosol canister 3.

The auxiliary spring 101 is a weak spring, incapable of returning the control lever 140 by itself. The spring force can be set to another force.

In order to complement the dimensional error of the aerosol canister 3, the metered dose inhaler of the Second Embodiment, as shown in FIGS. 20 and 21, is structured to include a control cap 200 formed of two components, an upper part and a lower part, which are assembled as follows. Note that the upper part is the bottom plate 200$b$1 of the cap portion 200$b$ of the control cap 200 and the lower part consists of the shell 200$b$2 of the cap portion 200$b$ of the control cap 200 and the junction member 20$a$.

In the last step of assembly, the aerosol canister 3 is inserted into the lower part and held therein as the valve stem 3$b$ is fitted to the fitting hole 2$b$1 (see FIG. 5) of the holder 2$b$. With no force applied to the aerosol canister 3, the capping, upper part is placed over the lower part. Upon recognition that the inner bottom face of the upper part is in contact with the bottom face of the aerosol canister 3, the upper part is bonded to the lower part by ultrasonic welding or other bonding means. The control cap 200 assembled this way can absorb the manufacturing error of the aerosol canister, for example, such as a large or small vertical dimension that does not conform to the designed dimension. These structures can be applicable to the below-mentioned embodiments.

The metered dose inhaler of the Second Embodiment further includes a lock mechanism that limits the depression displacement of the aerosol canister 3 when the mouthpiece cap is attached to the mouthpiece. The following describes the lock mechanism with reference to FIG. 20 through FIG. 28.

Referring to FIG. 20 through FIG. 25, the lower edge of the cap portion 200$b$ of the control cap 200 has raised portions 202 each having a slanted guide face 201 along the circumference of the cap portion 200$b$. Referring to FIG. 22 through FIG. 28, a lock member 300 is formed that includes upright portions 302 each having a slanted face 301 slidably guided by the slanted guide face 201. The lock member 300 also includes a rotational axis 303. The rotational axis 303 is inserted in a shaft hole 111 (see FIGS. 18 and 19) formed in the support member 110, so as to rotatably support the lock member 300 on the support member 110. When the control cap 200 is depressed, the slanted guide face 201 guides the slanted face 301, and the lock member 300 rotates as the slanted face 301 slides along the slanted guide face.

The lock member 300, as shown in FIG. 22, includes a lock portion 304 that interlocks with the protrusion 5$a$ to prevent movement of the slanted face 301. As shown in FIG. 22, at the position where the lock portion 304 prevents movement of the slanted face 301, the slanted face 301 supports the slanted guide face 201 to limit the depression displacement of the control cap 200. The movement of the slanted face 301 is allowed when the mouthpiece cap 5 is removed from the mouthpiece 4 (see FIG. 2) to release the protrusion 5a from the lock portion 304, as shown in FIGS. 24 and 25. When a compressive force is applied to the control cap 200, the slanted face 301 is displaced along the slanted guide face 201, and the upright portion 302 having the slanted face 301 moves into the recess 203 abutting on the raised portion 202, thereby allowing the depression displacement of the control cap 200. As described, in the Second Embodiment, the lock mechanism limits the depression displacement of the aerosol canister 3 when the mouthpiece cap 5 is attached to the mouthpiece 4. As described in the First Embodiment, when the mouthpiece cap 5 is attached, the depression displacement of the aerosol canister 3 is also limited by the protrusion 5a in contact with the tongue 20f (see FIG. 6) to prevent malfunction. Thus, the provision of the lock mechanism in the Second Embodiment gives extra safety to prevent malfunction.

Third Embodiment

The following will describe a Third Embodiment of a metered dose inhaler according to the present invention, with reference to FIG. 29 through FIG. 45.

The metered dose inhaler of this embodiment is used to directly deliver the aerosol medicament through the mouth of a patient. The external appearance is essentially the same as in the foregoing First and Second Embodiments. Specifically, as shown in FIG. 29, a metered dose inhaler 1 includes a housing body 2, and an aerosol canister 3 housed in the housing body 2, and a control cap 20 is affixed to the upper end of the aerosol canister 3. Further, as shown in FIG. 30, the housing body 2 includes a mouthpiece 4 put in the patient's mouth and a mouthpiece cap 5.

The aerosol canister 3 is as in the foregoing embodiments. Specifically, as shown in FIGS. 31 and 32, the aerosol canister 3 includes a substantially cylindrical, canister body 3a containing medicament, and a cylindrical bulge 3c of a small diameter is formed on a lower end face of the canister body 3a. The tubular, valve stem 3b extends downward from the bulge (step portion) 3c.

The housing body 2, as shown in FIG. 33, includes a cylindrical portion 2a providing an accommodation for the aerosol canister. The aerosol canister 3, as shown in FIG. 31, is inserted to the housing body 2 upside down, with the valve stem 3b facing downward. As shown in FIG. 33, the housing body 2 includes a holder 2b for holding the valve stem 3b. The holder 2b includes a fitting hole 2b1 formed to fit the valve stem 3b airtight. The housing body 2 further includes an orifice 2c, in communication with the fitting hole 2b1, and a funnel portion 2d in communication with the orifice 2c. Through the funnel portion 2d, the aerosol released from the valve stem 3b is guided into the mouthpiece 4.

Pressing down the canister body 3a of the aerosol canister 3 against the elastic force of the internal coil spring 500 pushes the valve stem 3b into the aerosol canister 3, opening the valve of the valve stem 3b. This causes the valve stem 3b to release the metered medicament-containing aerosol into the mouthpiece 4 through the orifice 2c and the funnel portion 2d.

As shown in FIGS. 31 and 32, the housing body 2 includes a dose counter 10, which counts the number of times the inhaler is used. The configuration of the dose counter 10 is as in the foregoing embodiments.

As shown by the enlarged, partial perspective view of FIG. 41, a control cap 20 includes a junction member 20a rotatably joined to the control lever 14, and a cap portion 20b which sheaths the canister body 3a from a bottom side of the canister body 3a. The structure of the junction member 20a differs from the foregoing embodiments.

The cap portion 20b may include a base plate 20b1, which can be brought into contact with the bottom of the aerosol canister, and a shell 20b2, surrounding the circumferential wall of the aerosol canister. The shell 20b2 includes cam followers 20c. The cam followers 20c engage cam grooves 2e (FIG. 29) formed on the inner circumferential surface of the housing body 2. The cam grooves 2e extend along the axial direction of the cylindrical portion 2a (FIG. 33) of the housing body 2 to guide the vertical, reciprocal movement of the control cap 20.

As shown in FIG. 41, the junction member 20a is a hooked (J-shape) member extending from the lower edge of the shell 20b2 of the cap portion 20b. As shown in FIGS. 38 and 39, the control lever 14 includes a link pin (protrusion) 14c between the locking pawl 14a and the hole 14b for receiving the shaft 11c. As shown in FIGS. 42 and 43, the control lever 14 is rotatably joined to the junction member 20a by the engagement of the junction member 20a with the link pin 14c. In the vertical movement of the junction member 20a, the link pin 14c does not engage the junction member 20a moving downward, whereas, in the upward movement, the junction member 20a engages the link pin 14c and moves with it, causing the control lever 14 to swing on the shaft 11c, as will be described later.

As shown in FIGS. 38 and 39, a horizontally extending, contact plate 14d is formed in the vicinity of the link pin 14c of the control lever 14, i.e., between the link pin 14c and the locking pawl 14a, to be brought into contact with the bulge 3c of the canister body 3a. The contact plate 14d, initially positioned between the tip of the valve stem 3b and the bulge 3c, is pushed by the bulge 3c as the canister body 3a lowers by the depression of the control cap 20, causing the control lever 14 to swing on the shaft 11c. The control lever 14, as shown in FIGS. 38 and 39, includes a stopper 14s, which prevents the display members 12 and 13 from rotating by accident when the control lever 14 is not swinging. Such a structure to prevent the rotation of the display members are the same as the first embodiment.

The housing body 2 also includes a through-hole 2g (FIG. 33) through which the protrusion 5a penetrates into the housing body 2 when the mouthpiece cap 5 is attached to the mouthpiece 4. This structure is as in the foregoing embodiments and will not be described further.

The following describes an operation of the metered dose inhaler structured as above, with reference to FIGS. 42 and 43. Actuation of the metered dose inhaler requires removal of the mouthpiece cap 5 from the mouthpiece 4.

FIG. 42 is a partial, cutaway perspective view showing an initial state before the canister body 3a is depressed into of the housing 2. In this state, the stopper 14s is in engagement with the display member 12, 13 to prevent malfunction of the display member 12, 13. FIG. 43 is a partial, cutaway perspective view showing the canister body 3a depressed inside the housing 2.

After taking off the mouthpiece cap 5, a patient puts the mouthpiece 4 in the mouth, or supports it in front of the mouth. The patient then manually depresses the canister body 3a of the aerosol canister 3, via the cap portion 20b, into the housing 2 against the internal coil spring 500. This causes the bulge 3c of the canister body 3a to engage the contact plate 14d and pushes down the contact plate 14d as the canister body 3a moves downward. As a result, the control lever 14 swings downward, from the position shown in FIG. 42 to the lower position shown in FIG. 43. At the lower position, the locking pawl 14a of the control lever 14 interlocks with one of the locking grooves 13c of the display member 13 (see also FIG. 38). Here, the junction member 20a, joined to the cap portion 20b, also moves downward by the depression. However, since the control lever 14 swings downward, the junction member 20a and the link pin 14c of the control lever 14 both move downward, without engaging each other.

When the canister body 3a of the aerosol canister 3 is depressed into the housing body 2, the valve stem 3b releases the medicament-containing aerosol. Out of the valve stem 3b, the medicament-containing aerosol is released outside through the orifice 2c, the funnel portion 2d, and the mouthpiece 4 (see also FIG. 33).

After the medicament-containing aerosol is released, the compressive force exerted on the canister body 3a via the cap portion 20b is released. In response, the internal coil spring of the aerosol canister 3 pushes back the control cap 20 with the canister body 3a. As the control cap 20 is pushed back, the junction member 20a of the control cap 20 engages the link pin 14c and moves upward with the link pin 14c. As a result, the control lever 14 swings back to the original position shown in FIG. 42, from the lower position shown in FIG. 43. When the control lever 14 returns to the original position, the locking pawl 14a interlocking with one of the locking grooves 13c causes the display member 13 to rotate by a predetermined angle. This predetermined angle of rotation is the angle required to cause the display of the display member 13 to increment one. Note that, with the canister body 3a back to original position, the valve stem 3b returns to the original position and the medicament is filled for the next injection.

As described above, in this embodiment, the control lever 14 is sprung back by the internal coil spring of the aerosol canister 3. Thus, the structure of the metered dose inhaler can be simple. Note that the auxiliary spring can be mounted as shown in the second embodiment.

Often, there is variation in the length of the valve stem due to manufacturing error of the aerosol canister. For example, as shown in FIG. 44, an aerosol canister with a longer valve stem (FIG. 44(a)) tends to require a longer depression distance for the valve stem, from the point of depression to the release of the contents, compared with an aerosol canister with a shorter valve stem (FIG. 44(b)) requiring a shorter depression distance.

By contrast, in the present embodiment, the contact plate 14d is provided for the control lever, at a predetermined position between the bulge 3c of the canister body 3a and the tip of the valve stem 3b. This is advantageous in the following respect. For example, as shown in FIG. 45, consider an aerosol canister with a longer valve stem (FIG. 45(a)) and an aerosol canister with a shorter valve stem (FIG. 45(b)). By comparing these two aerosol canisters, while the depression distance differs until the canister at the initial position hits the contact plate, the depression distances (a and b) are essentially the same from the contact point to the release position. This is because the valve stems having different lengths have different depression distances, as noted above. Since the contact plate 14d is displaced over substantially the same depression distance to the release position, the locking pawl 14a engages with the locking groove 13c at substantially the same timing as the ejection of the medicament even though the aerosol canisters have different lengths of the valve stem 3b. Accordingly, the update of the dose counter 10 and the ejection will be made at substantially the same timing the between these aerosol canisters. That is, the release timing of the medicament, and the update timing of the dose counter will be substantially the same between the both aerosol canisters even when there is variation in the length of the valve stem 3b, so that the patient will not notice a time lag due to a difference in length of the valve stem.

Fourth Embodiment

The following will describe a Fourth Embodiment of the present invention. The Fourth Embodiment, being a modification of the Third Embodiment, will be described concerning elements that differ from the Third Embodiment. First, as shown in FIG. 46, in the control cap 20b, the shell 20b2 surrounding the outer circumferential face of the aerosol canister 3 has a plurality of ribs 20r formed on its lower end along the circumference. The ribs 20r radially extend to support the aerosol canister 3. During assembly, the shell 20b2 is installed first in the housing 2, and then the aerosol canister 3 is disposed inside the shell 20b2. Without the ribs 20r, the aerosol canister 3 may move downward, causing the dose counter to advance. There are cases where the dose counter is advanced when the inhaler is dropped and the aerosol canister 3 is moved downward by the force of impact. In the present embodiment, the provision of the ribs 20r enables the aerosol canister 3 to be supported by the ribs 20r so that the aerosol canister 3 does not move downward unless the base plate 20b1 is pressed. This prevents the medicament-containing aerosol from being released or the dose counter from advancing accidentally.

The structure of the dose counter is explained below. In the present embodiment, the structures of the display member 13 and the control lever 14 differ from those in the First Embodiment. As shown in FIGS. 47 and 48, no recesses are formed in the circumference of the display member 13. Instead, a plurality of raised portions 13y are formed equiangularly on the circumferential surface of the display member 13 that faces the control lever 14. As shown in FIG. 49, a protrusion 14f is formed in a middle portion of the control lever 14, in such a manner that the protrusion is capable of engaging the raised portions 13y. The stopper 14s of the control lever 14 is also provided with a protrusion 14s2, which engage the raised portions 13y. In the initial state as shown in FIG. 42, since each of the protrusions 14s2 engages each raised portion 13y, rotation of the display member 13 is restricted. If the inhaler is dropped in this state, the interlock between the protrusions 14s2 and the raised portions 13y may be released upon impact. When the control lever 14 rotates in the direction to release their engagement, the protrusion 14f of the control lever 14 engages one of the raised portions 13y of the display member 13, as shown in FIG. 49, to prevent rotation of the display member 13. Accordingly, the structure of the present embodiment can prevent the rotation of the display member 13 when the inhaler is not used.

While the foregoing described embodiments of the present invention, the invention is not limited by the implementation discussed above, and may be applied in many variations within the scope of the present invention. For example, while the Third Embodiment described a configuration in which the bulge of the aerosol canister engages the contact plate, at least a portion of the aerosol canister is required to engage the contact plate, and the portion making contact with the contact plate is not particularly limited. That is, the portion of the aerosol canister engaging the contact plate or the control lever may be an end face or an outer circumferential surface of the canister body of the aerosol canister, so that the contact plate or the control lever can move with the aerosol canister.

Further, the aerosol canister is not necessarily required to engage the contact plate, and may engage any part of the control lever, as long as it can move the control lever. Further, the control lever is not necessarily required to swing as long as it can move between at least two positions. Specifically, the control lever is not limited to a particular configuration as long as it can move between the initial position and the depressed position to update the dose counter when returning to the initial position from the depressed position, and move with the junction member of the control cap when returning to the initial position.

Further, an auxiliary spring may be provided that helps the aerosol canister return to the initial position. For example, the auxiliary spring may be coiled around the shaft 11c of the dose counter 10. In this way, since the control lever 14 is moved to the depressed position against the auxiliary spring, the force of the auxiliary spring combines with the force of the spring of the aerosol canister when the aerosol canister returns to the initial position, ensuring that the aerosol canister returns to the initial position without fail. In addition, as long as the auxiliary spring can assist to return the aerosol canister to the original position, the spring can be mounted in other locations. For example, the spring can be mounted between the housing body 2 and the bulge 3c of the aerosol canister 2, or between the bottom plate 20b1 of the cap portion and the bottom of the canister body 3a. The dose counter of the above embodiment is count-up type, but the numbers of the display members 12, 13 can be rearranged for count-down type dose counter.

Further, while the Third Embodiment described the dose counter that comes into operation while the control cap returns to the initial position from the depressed position, the dose counter may alternatively be operated while the control cap is moved to the depressed position from the initial position.

BRIEF DESCRIPTION OF THE DRAWINGS

FIG. 50 is an explanatory diagram of FIG. 1.

FIG. 51 is an explanatory diagram of FIG. 1 having the spring compressed.

FIG. 52 is another view of the interior of the assembly of FIG. 3.

FIG. 53 is a cutaway view of FIG. 4.

REFERENCE NUMERALS

Figure 1:
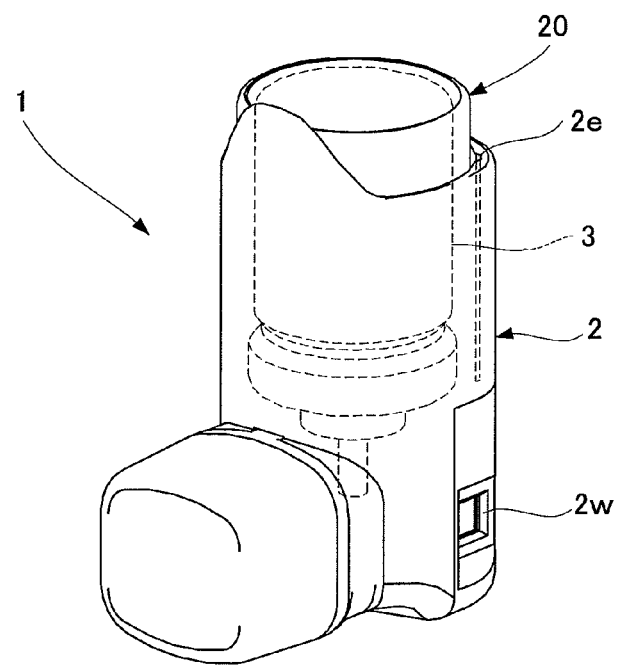
FIG. 1 is a perspective view showing a First Embodiment of a metered dose inhaler according to the present invention.
Figure 2:
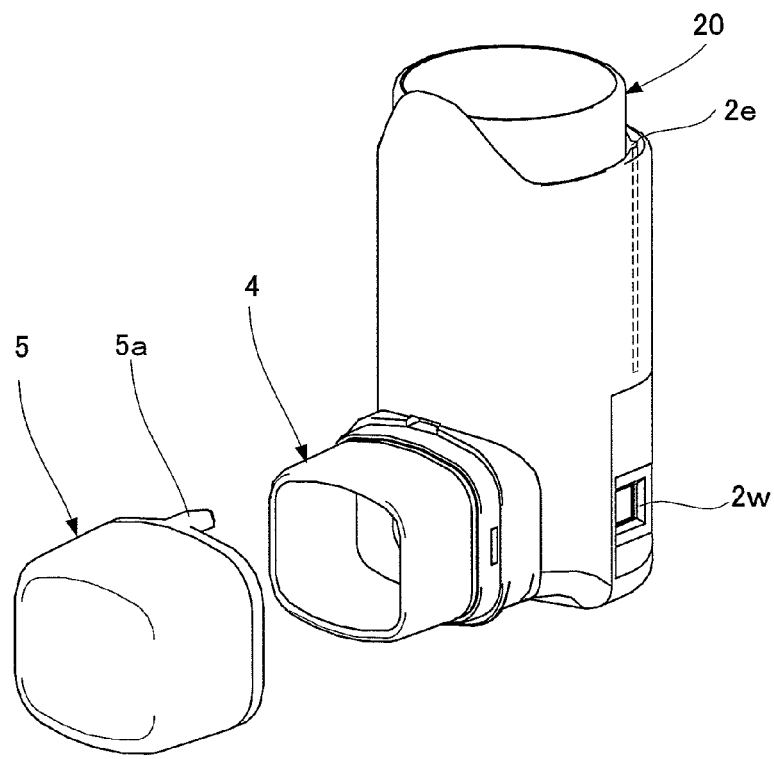
FIG. 2 is a perspective view showing a state in which a mouthpiece cap is removed from the metered dose inhaler of FIG. 1.
Figure 3:
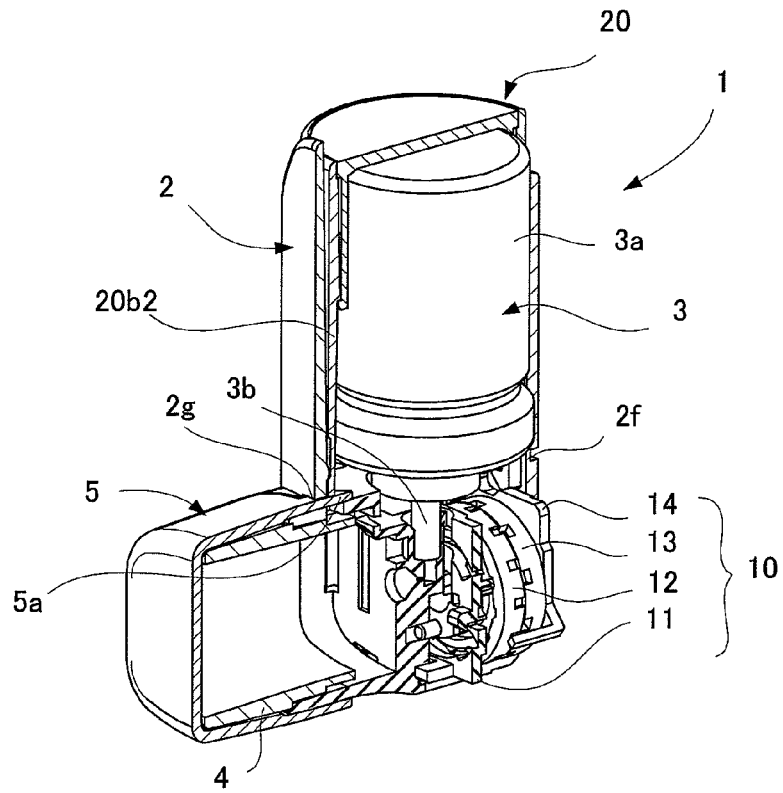
FIG. 3 is a perspective view showing a partial cutaway illustration of FIG. 1.
Figure 4:
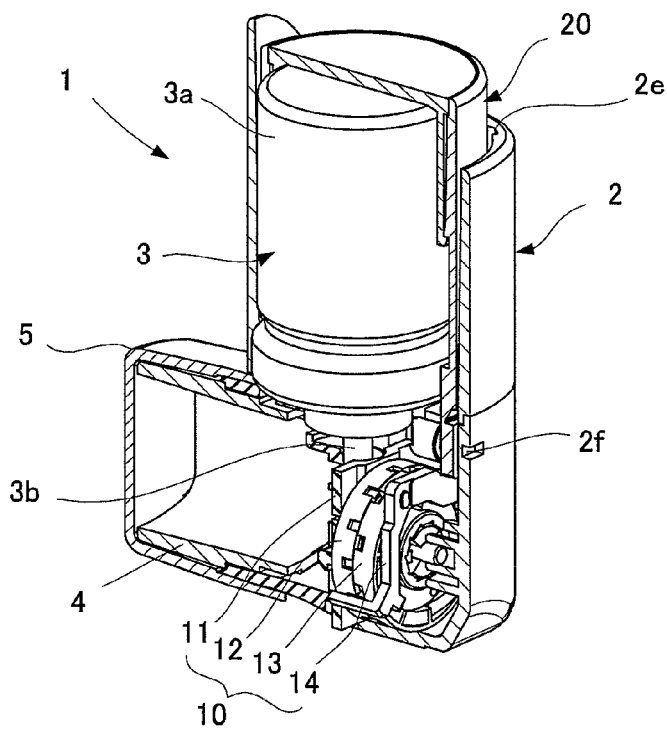
FIG. 4 is a perspective view showing FIG. 3 from another angle.
Figure 5:
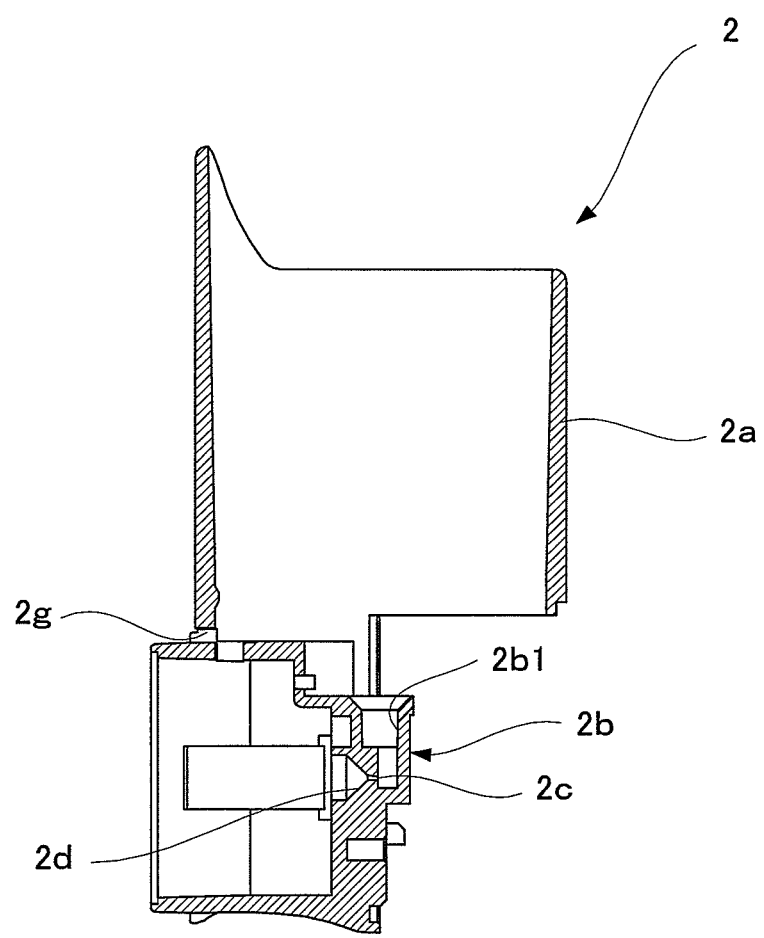
FIG. 5 is a part sectioned, longitudinal view of the metered dose inhaler of FIG. 1.
Figure 6:
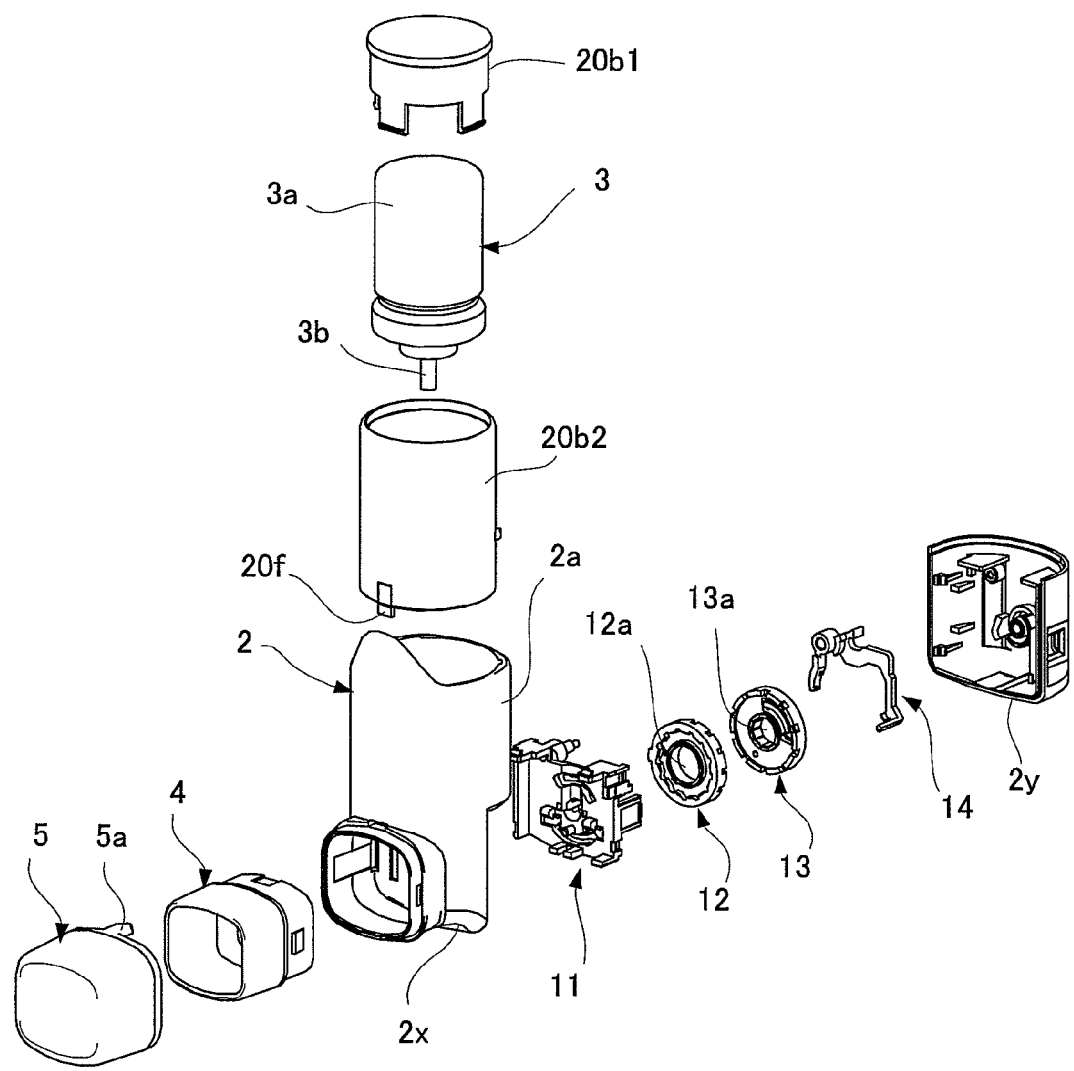
FIG. 6 is an exploded, perspective view of the metered dose inhaler of FIG. 1.
Figure 7:
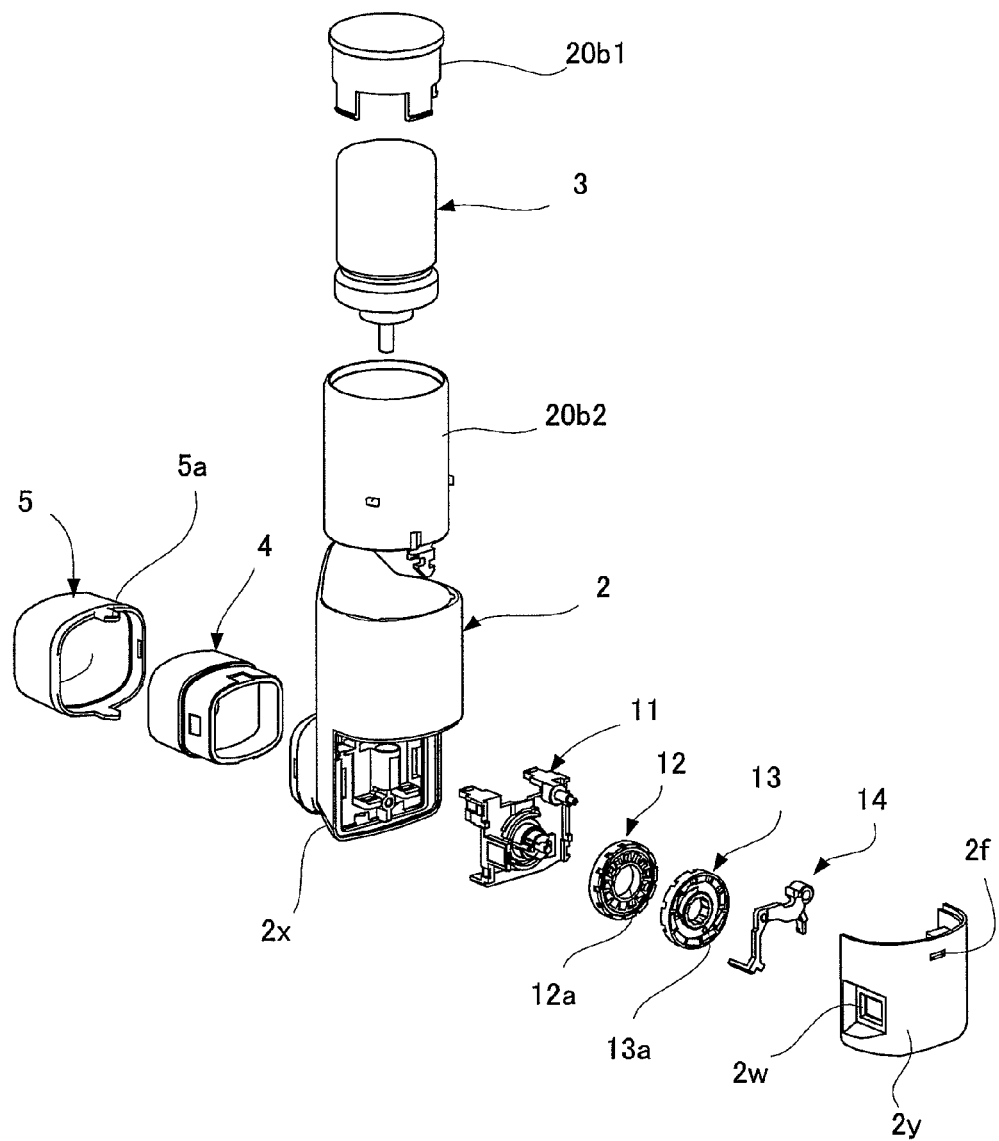
FIG. 7 is a perspective view showing FIG. 6 from another angle.
Figure 8:
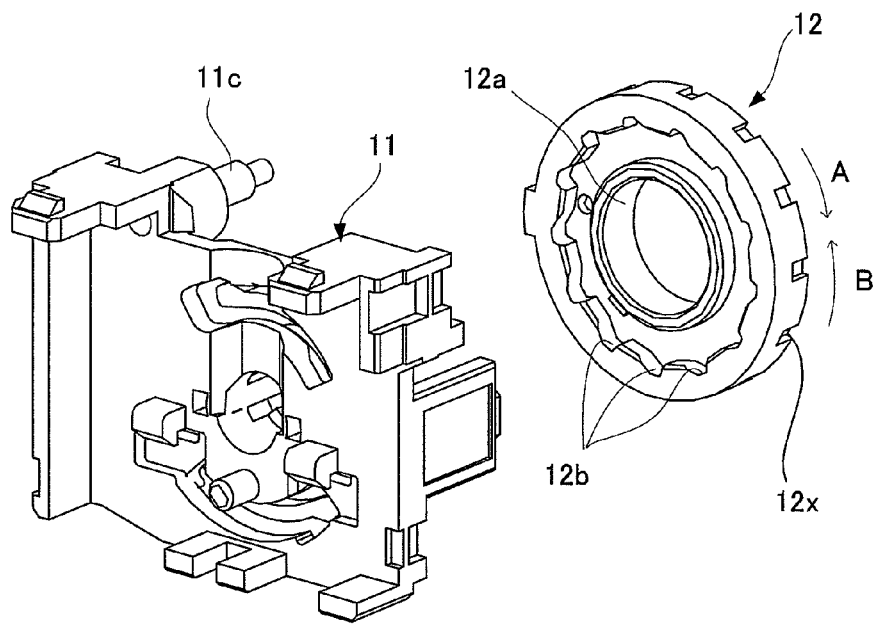
FIG. 8 is a partially enlarged, perspective view of FIG. 6.
Figure 9:
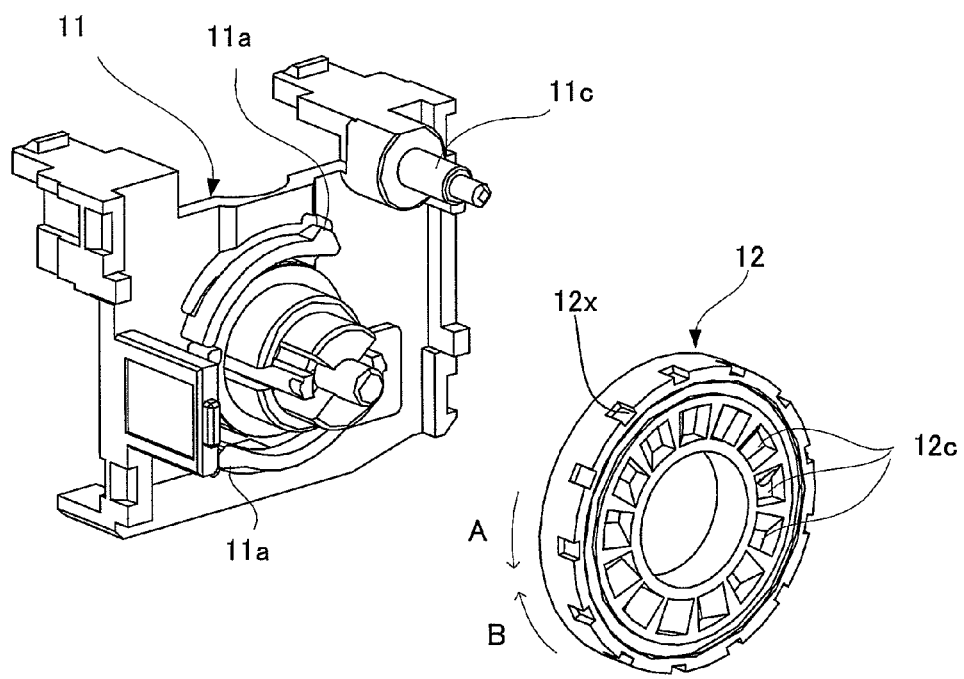
FIG. 9 is a partially enlarged, perspective view of FIG. 7.
Figure 10:
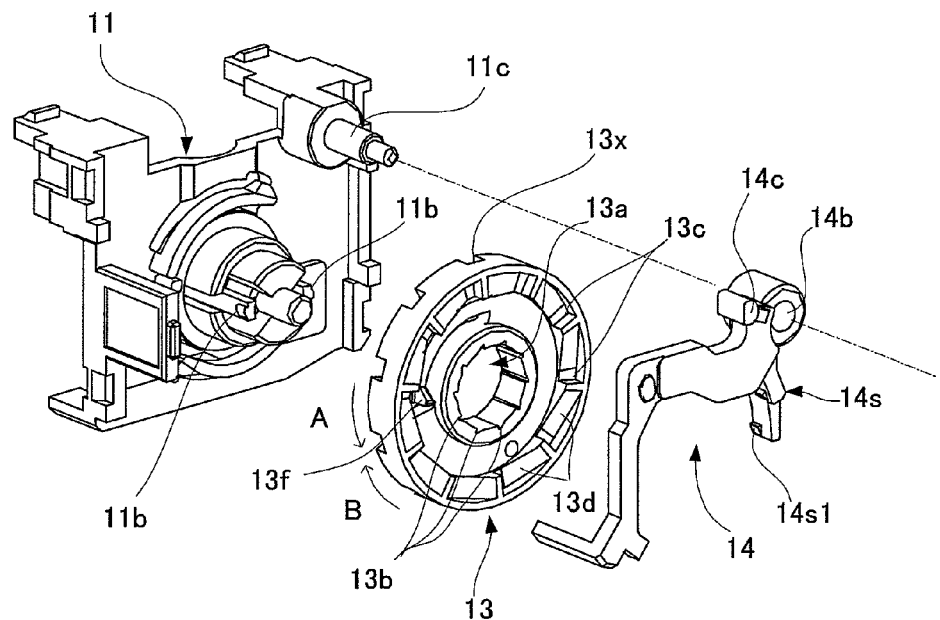
FIG. 10 is another partially enlarged, perspective view of FIG. 7.
Figure 11:
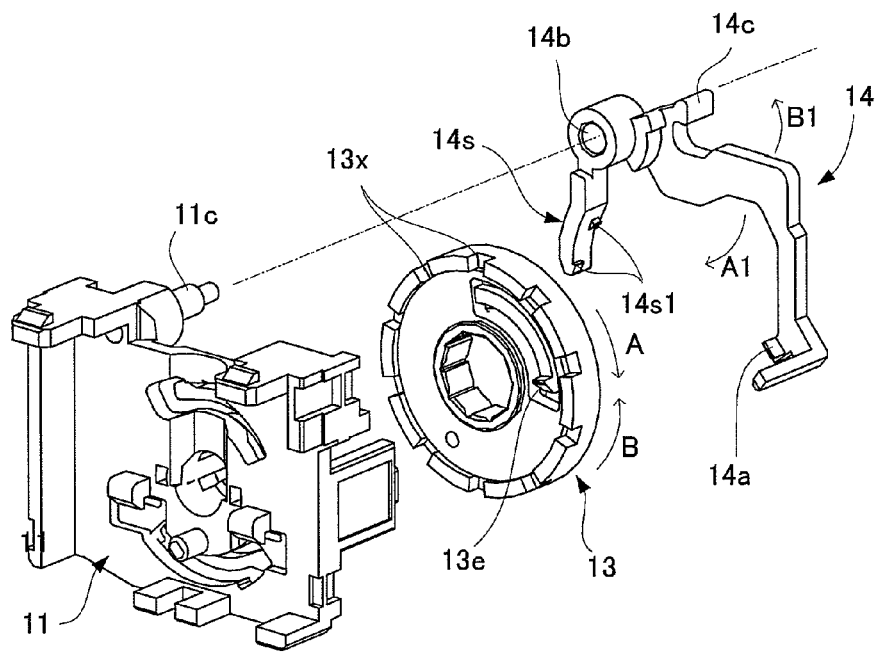
FIG. 11 is another partially enlarged, perspective view of FIG. 6.
Figure 12:
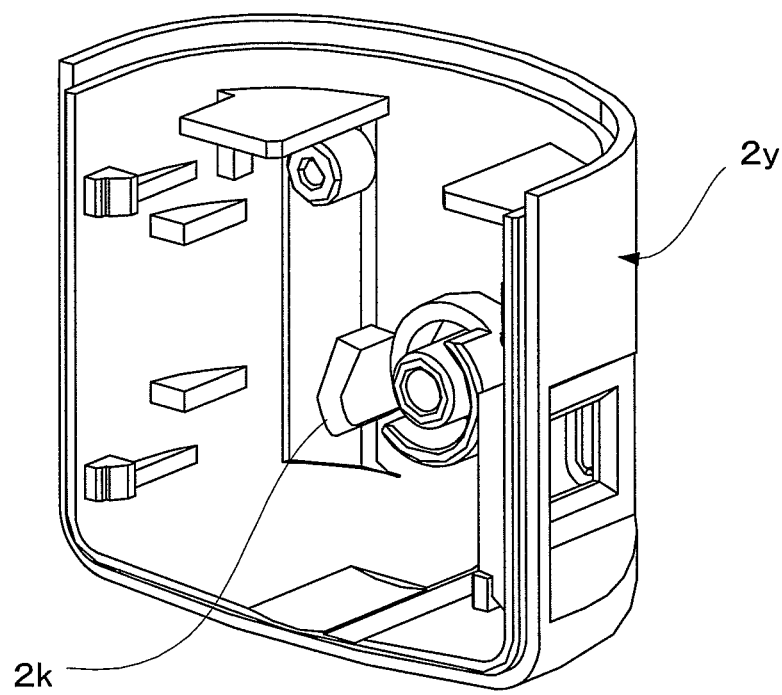
FIG. 12 is still another partially enlarged, perspective view of FIG. 6.
Figure 13:
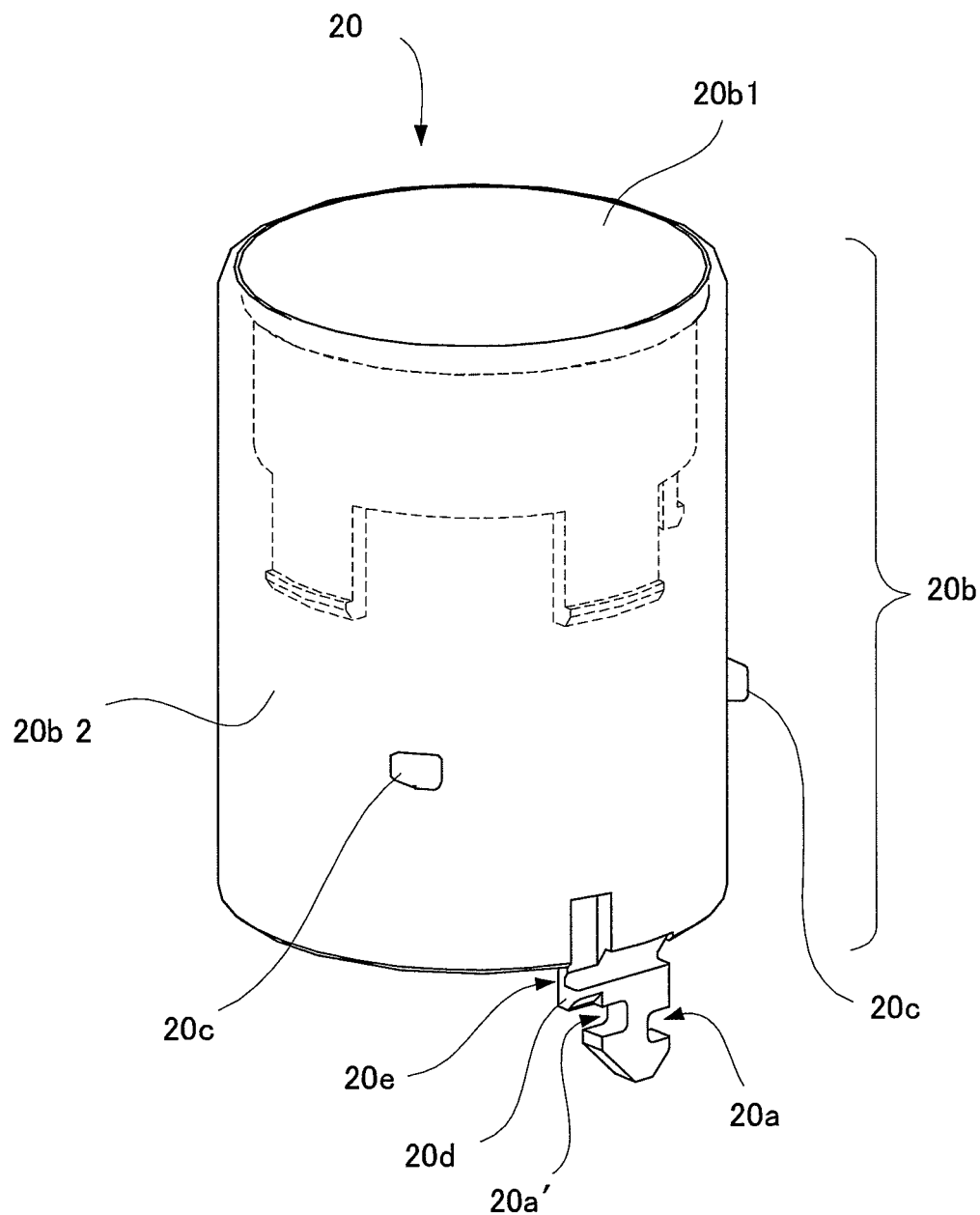
FIG. 13 is an enlarged, partial perspective view showing a control cap of FIG. 7 after assembly.
Figure 14:
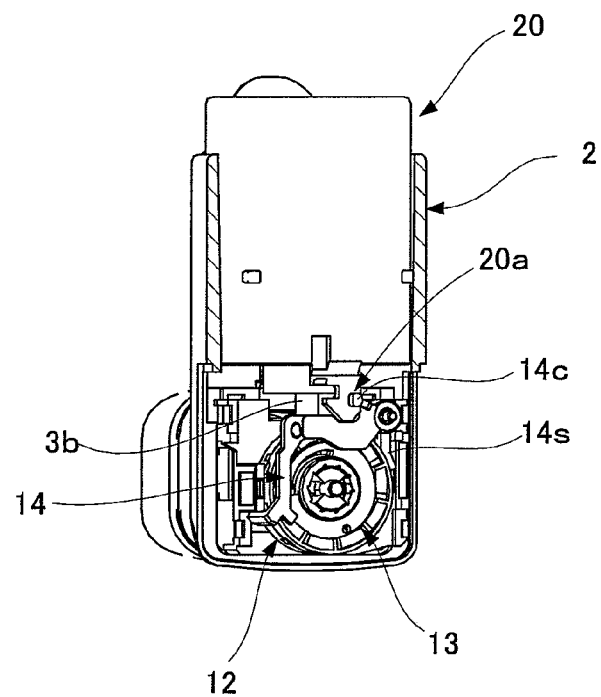
FIG. 14 is a part sectioned, perspective view of the metered dose inhaler of FIG. 1.
Figure 15:
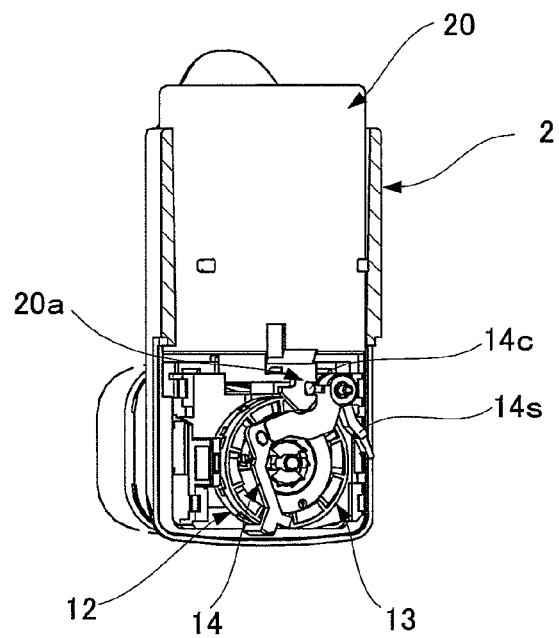
FIG. 15 is a perspective view showing an operational state following FIG. 14.
Figure 16:
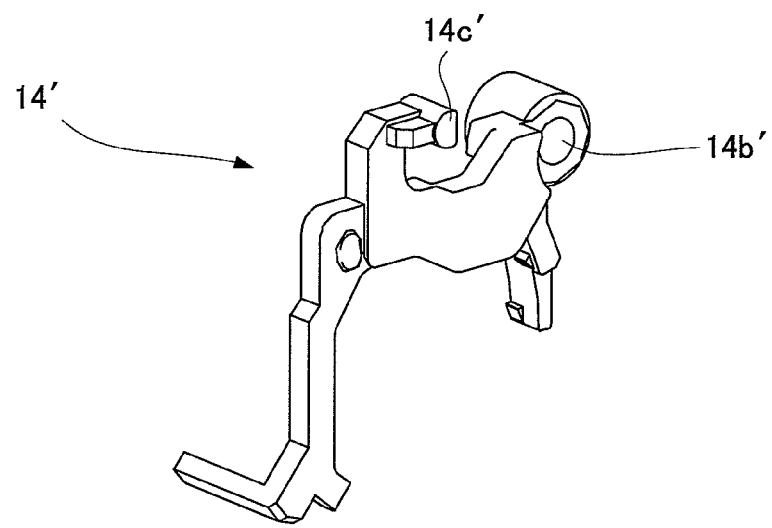
FIG. 16 is a perspective view showing another form of a control lever as a constitutional element of a metered dose inhaler according to the present invention.
Figure 17:
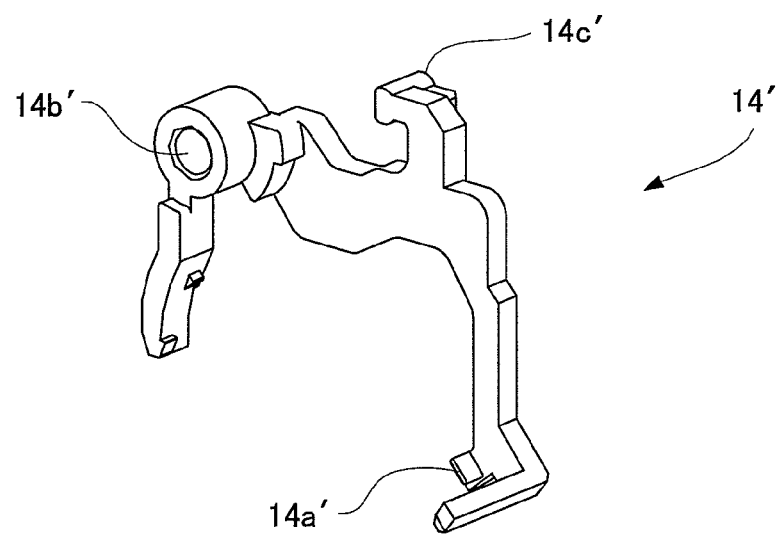
FIG. 17 is a perspective view showing the control lever of FIG. 16 as viewed from another direction.
Figure 18:
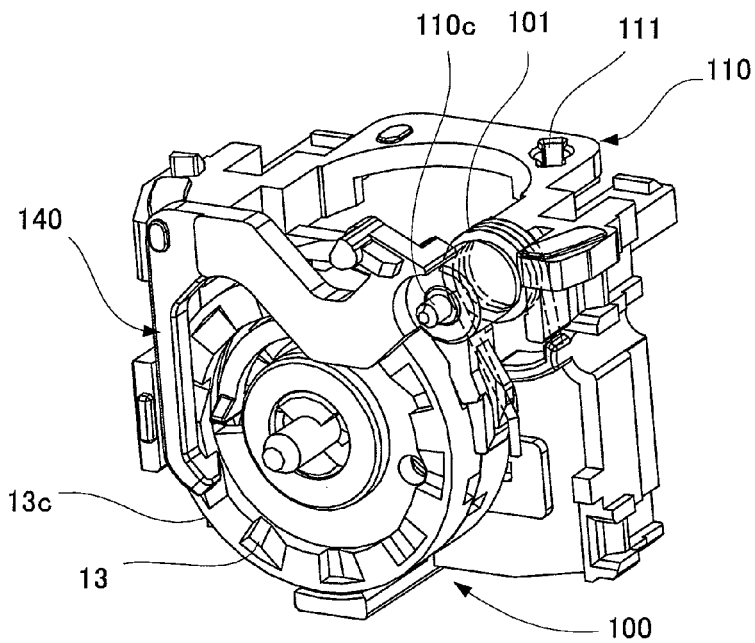
FIG. 18 is a partially enlarged, perspective view showing a Second Embodiment of a metered dose inhaler according to the present invention.
Figure 19:
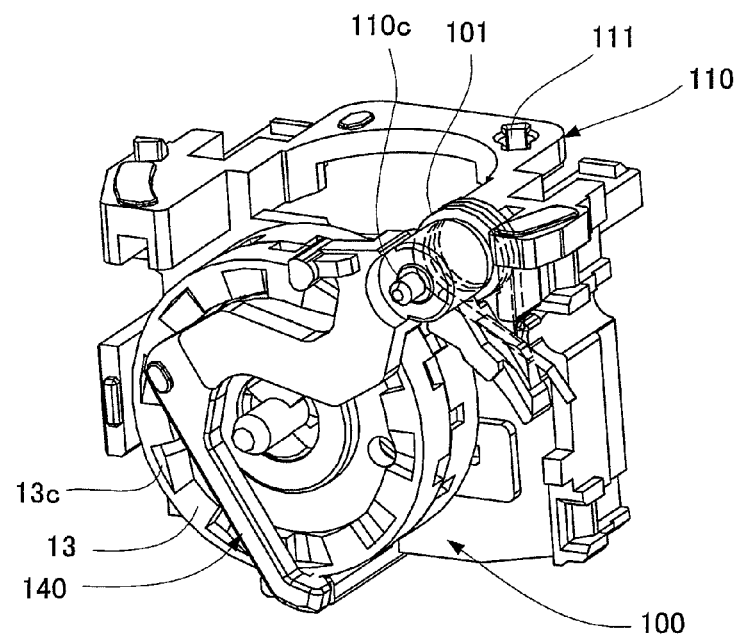
FIG. 19 is a perspective view showing an operational state following FIG. 18.
Figure 20:
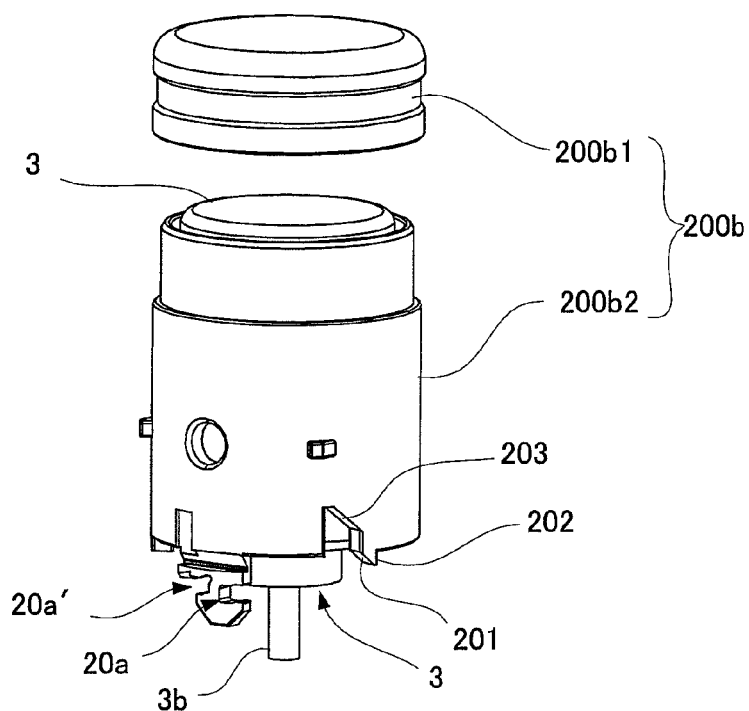
FIG. 20 is another partially enlarged, perspective view showing a Second Embodiment of a metered dose inhaler according to the present invention.
Figure 21:
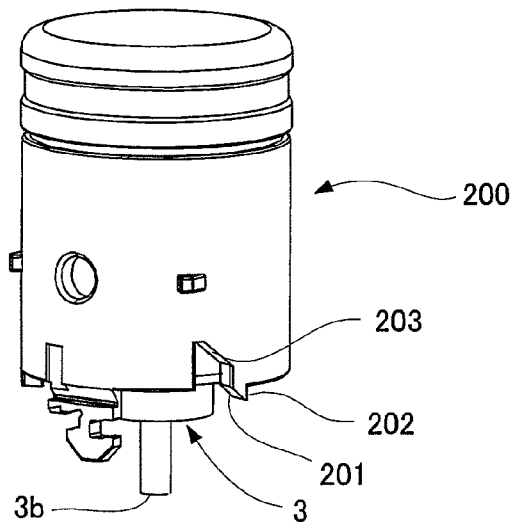
FIG. 21 is a perspective view showing an assembly step following FIG. 20.
Figure 22:
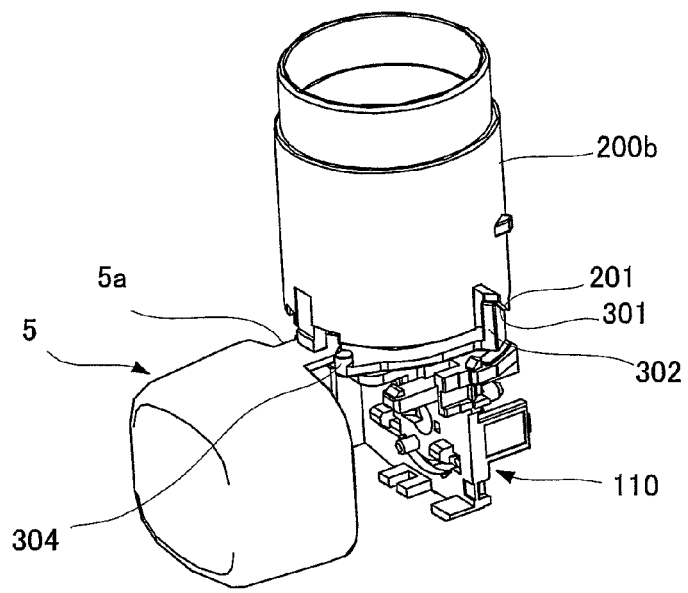
FIG. 22 is a partially enlarged, perspective view showing a Second Embodiment of a metered dose inhaler according to the present invention.
Figure 23:
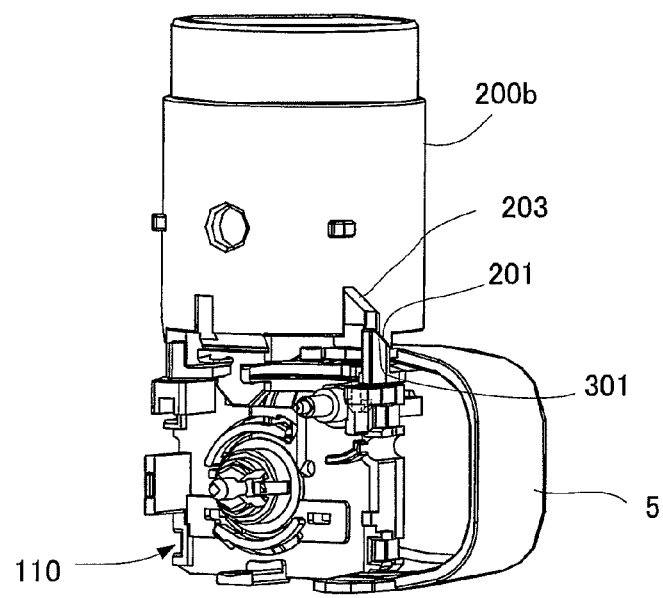
FIG. 23 is a perspective view showing FIG. 22 from another angle.
Figure 24:
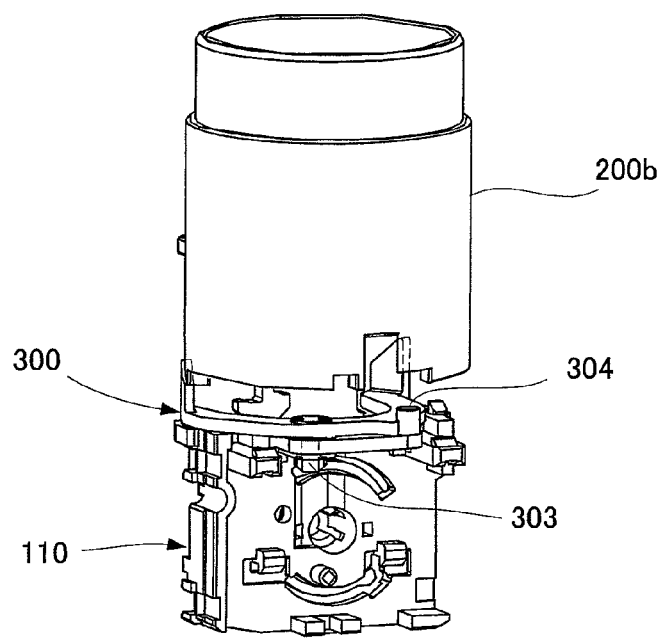
FIG. 24 is a perspective view showing FIG. 22 from another angle with a mouthpiece cap removed.
Figure 25:
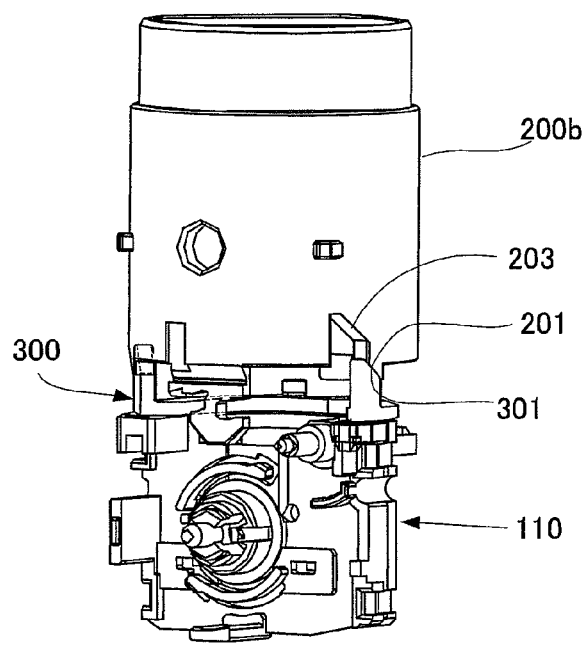
FIG. 25 is a perspective view showing FIG. 24 from another angle.
Figure 26:
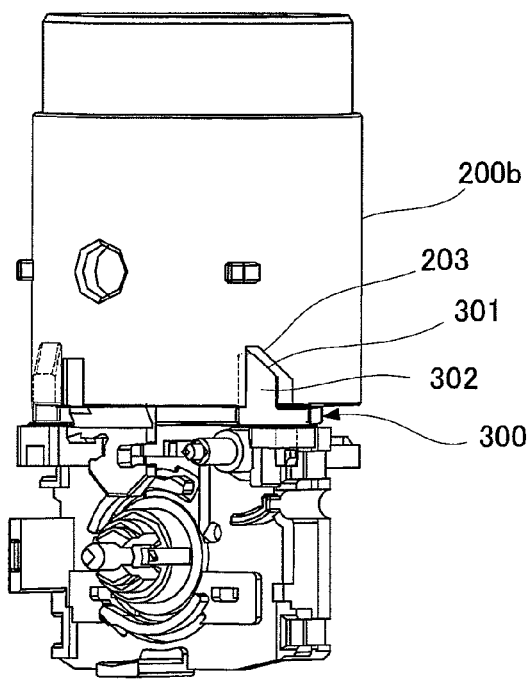
FIG. 26 is a perspective view showing an operational state following FIG. 25.
Figure 27:
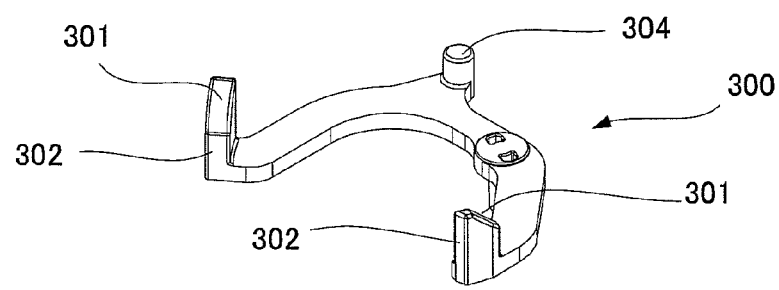
FIG. 27 is an enlarged, perspective view of a lock member included in FIG. 22.
Figure 28:
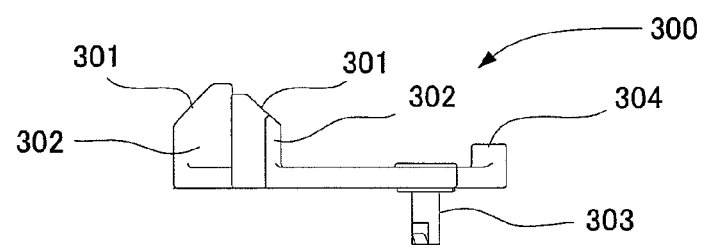
FIG. 28 is a side view of the lock member shown in FIG. 27.
Figure 29:
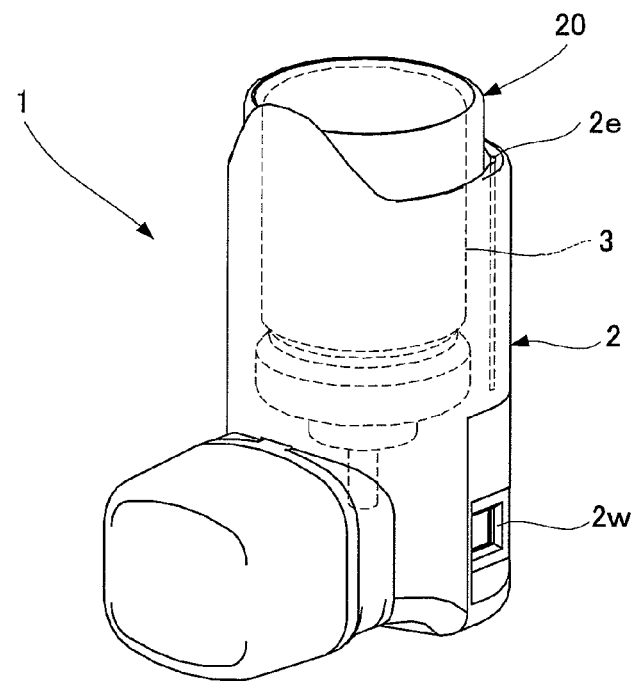
FIG. 29 is a perspective view showing a Third Embodiment of a metered dose inhaler according to the present invention.
Figure 30:
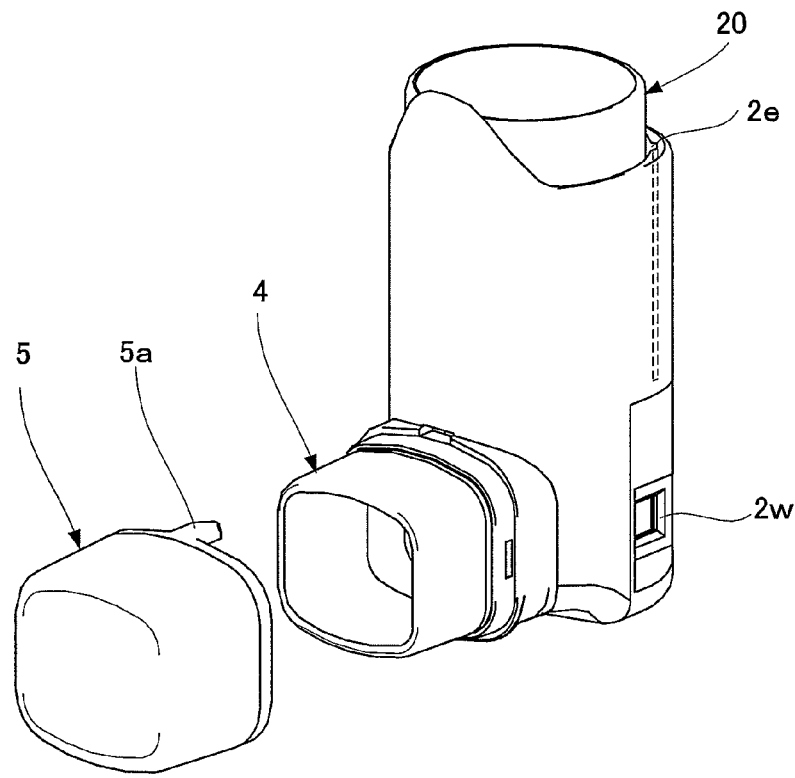
FIG. 30 is a perspective view showing a state in which a mouthpiece cap is removed from the metered dose inhaler of FIG. 29.
Figure 31:
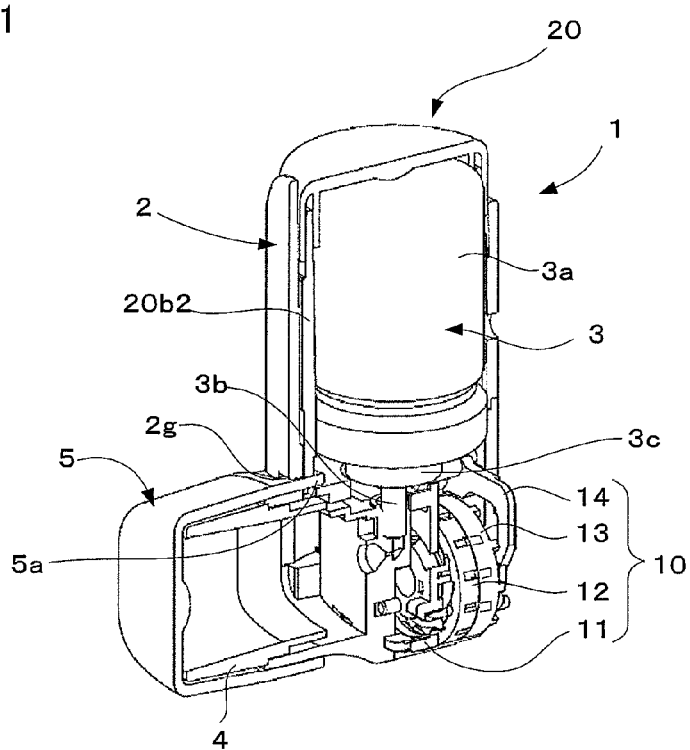
FIG. 31 is a perspective view showing a partial cutaway illustration of FIG. 29.
Figure 32:
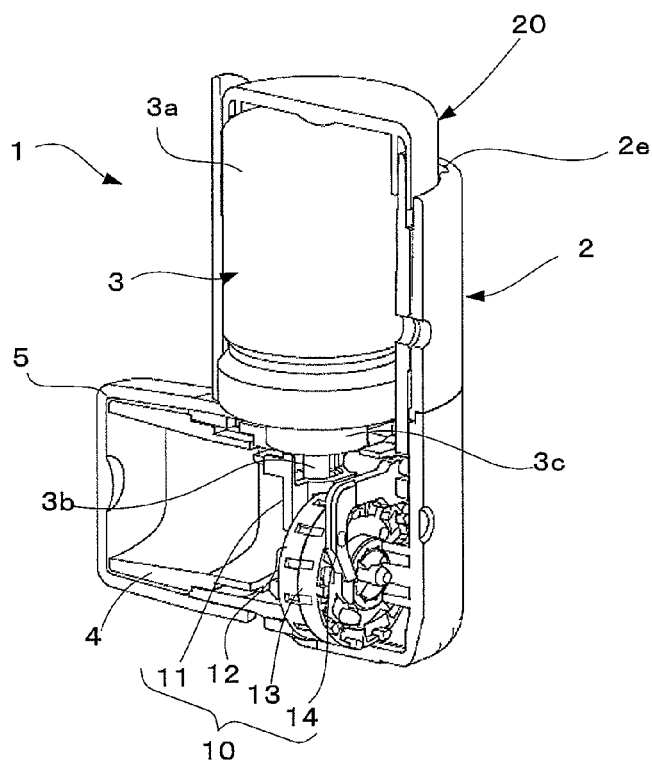
FIG. 32 is a perspective view showing FIG. 31 from another angle.
Figure 33:
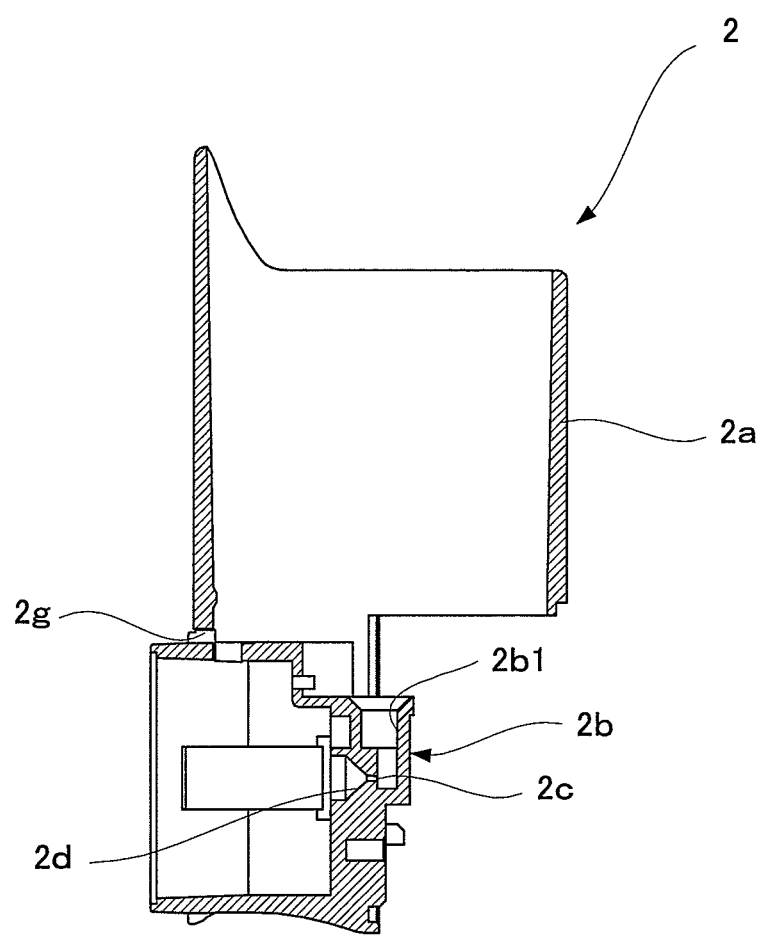
FIG. 33 is a part sectioned, longitudinal view of the metered dose inhaler of FIG. 29.
Figure 34:
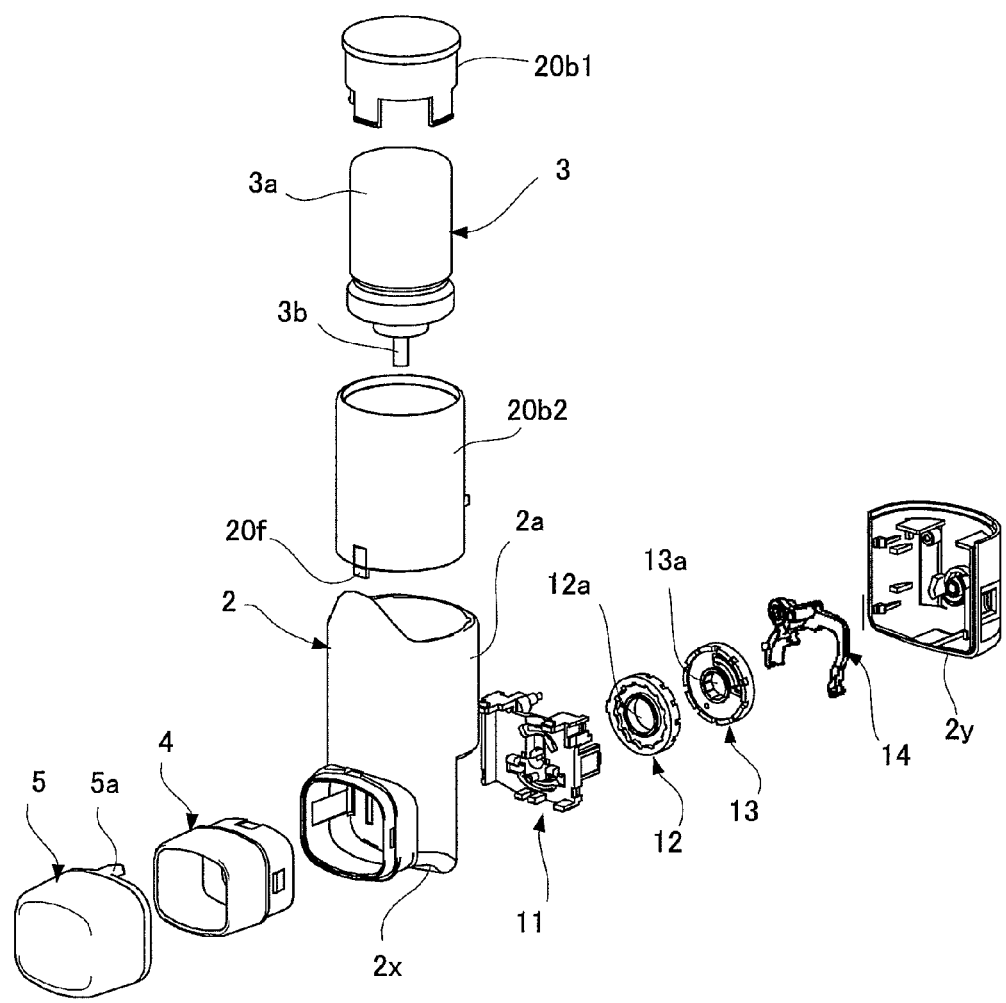
FIG. 34 is an exploded, perspective view of the metered dose inhaler of FIG. 29.
Figure 35:
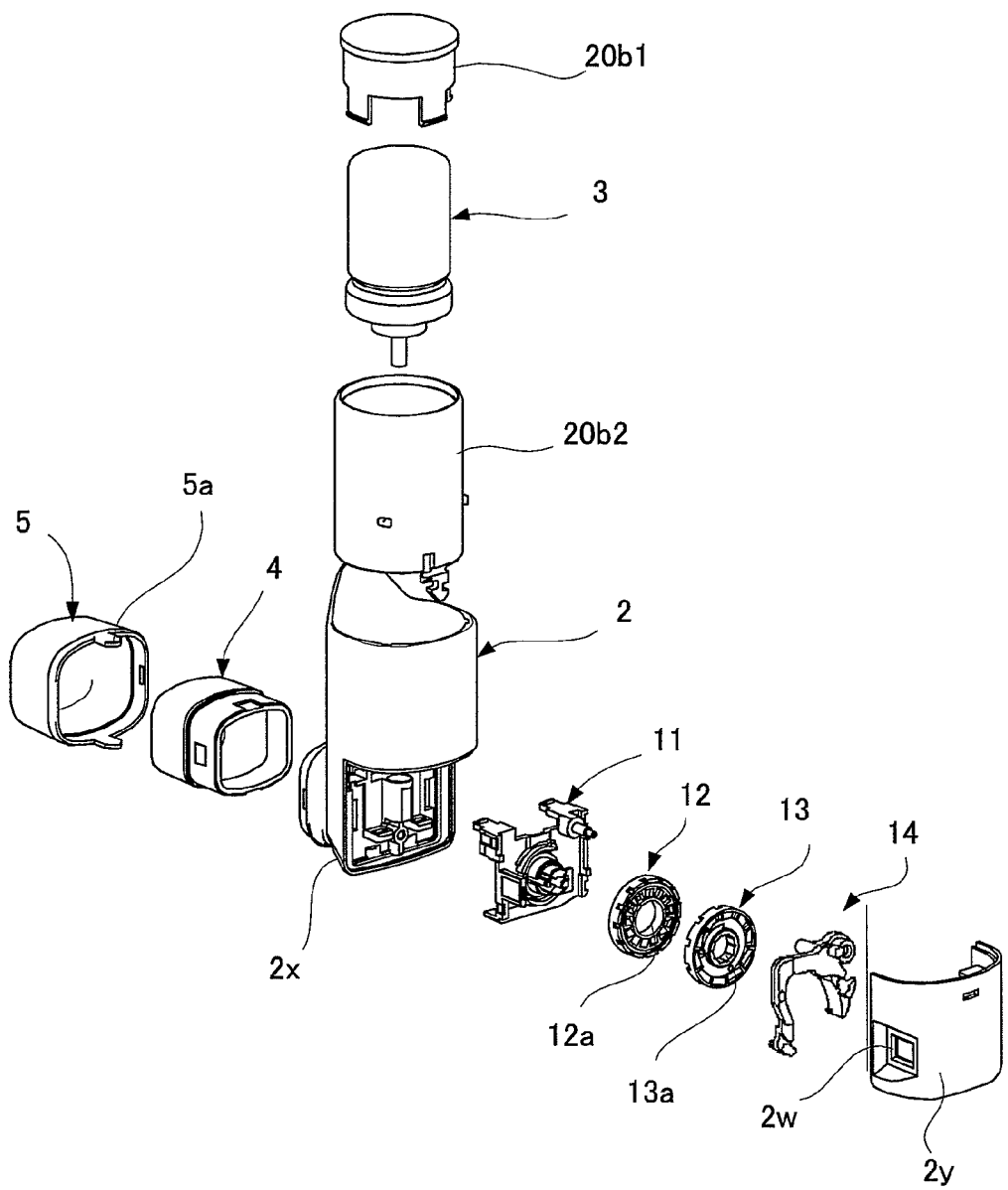
FIG. 35 is a perspective view showing FIG. 34 from another angle.
Figure 36:
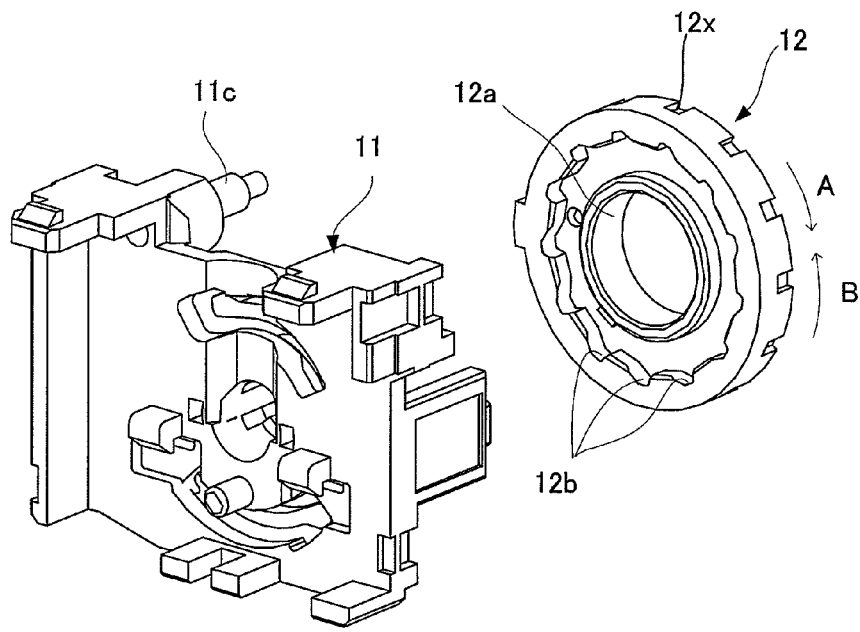
FIG. 36 is a partially enlarged, perspective view of FIG. 34.
Figure 37:
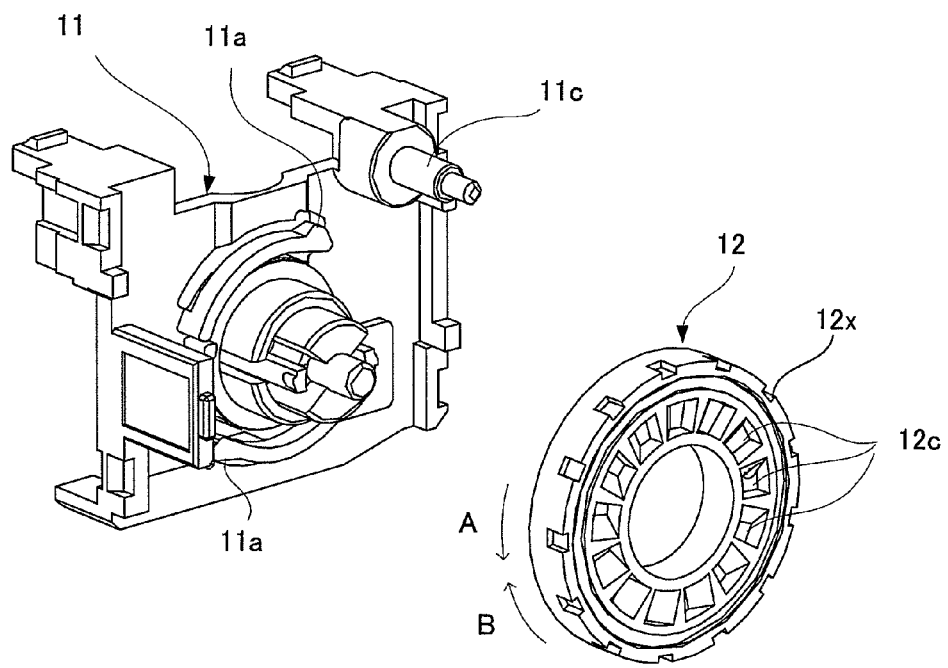
FIG. 37 is a partially enlarged, perspective view of FIG. 35.
Figure 38:
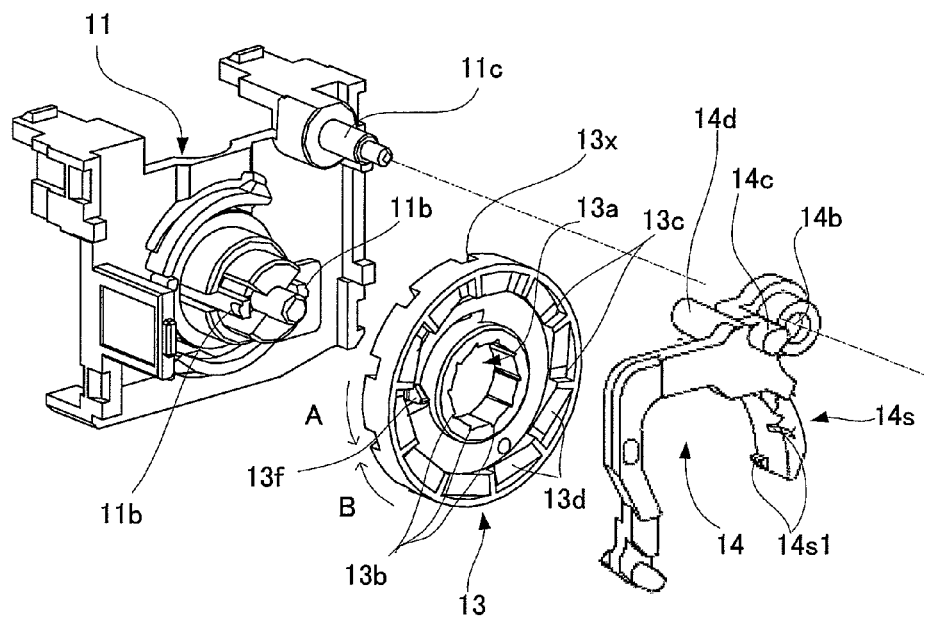
FIG. 38 is another partially enlarged, perspective view of FIG. 35.
Figure 39:
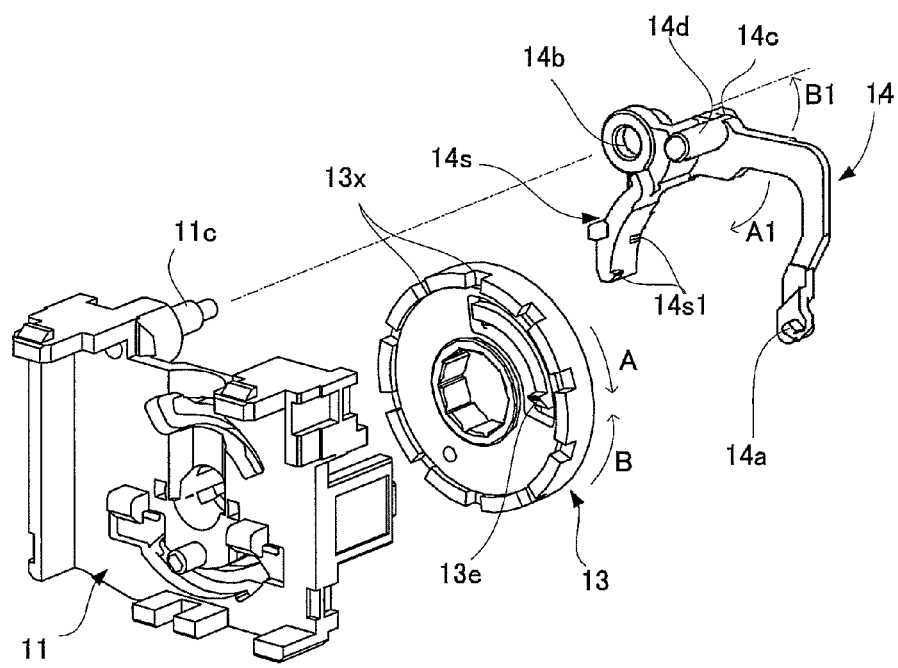
FIG. 39 is another partially enlarged, perspective view of FIG. 34.
Figure 40:
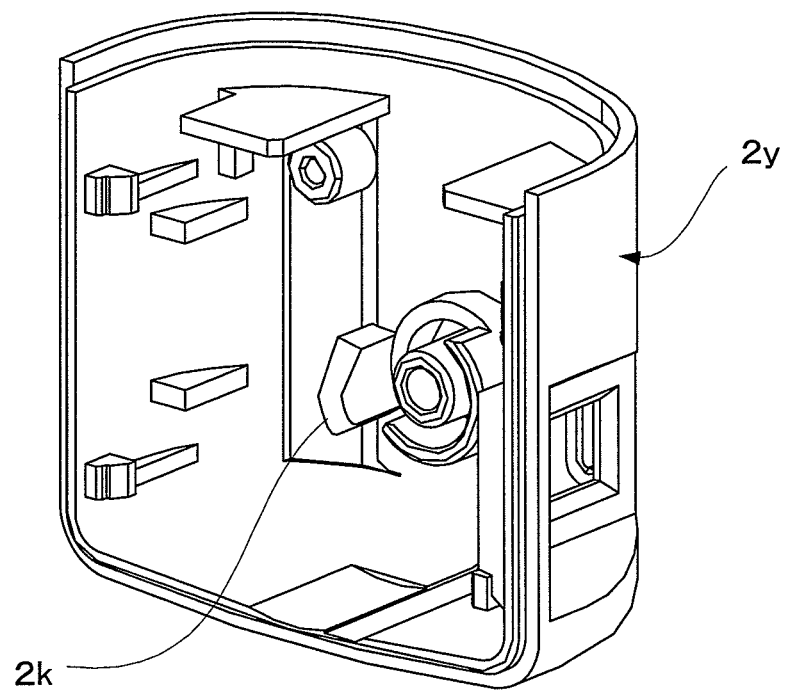
FIG. 40 is still another partially enlarged, perspective view of FIG. 34.
Figure 41:
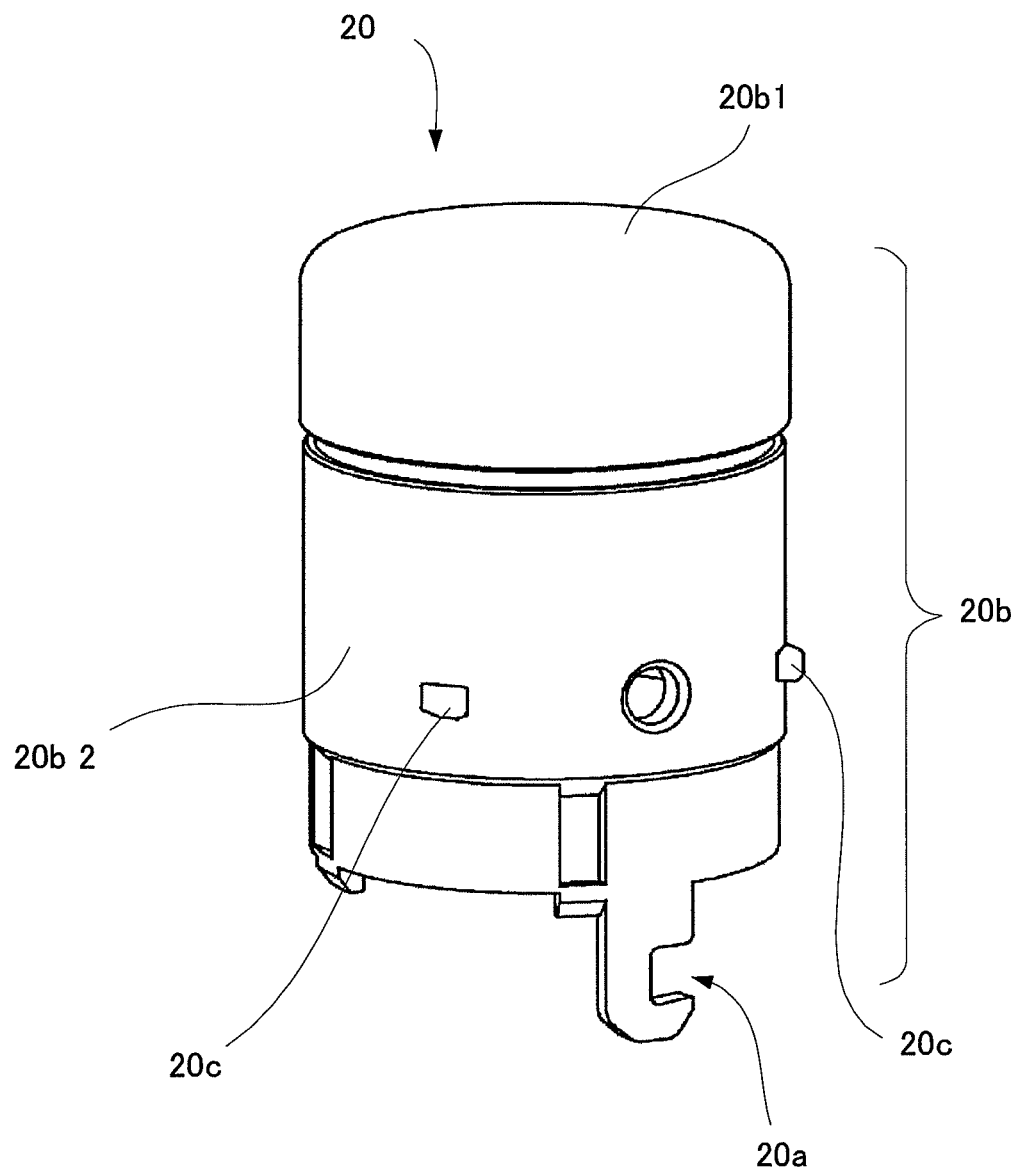
FIG. 41 is an enlarged, perspective view showing a control cap of FIG. 35 after assembly.
Figure 42:
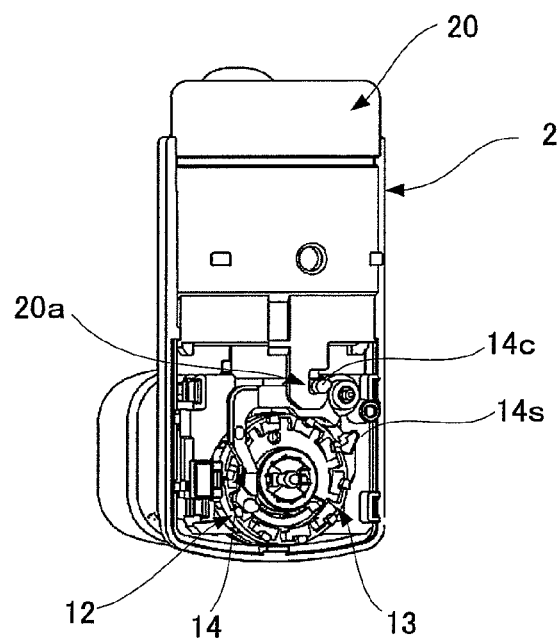
FIG. 42 a perspective view showing a partial cutaway illustration of the metered dose inhaler of FIG. 29.
Figure 43:
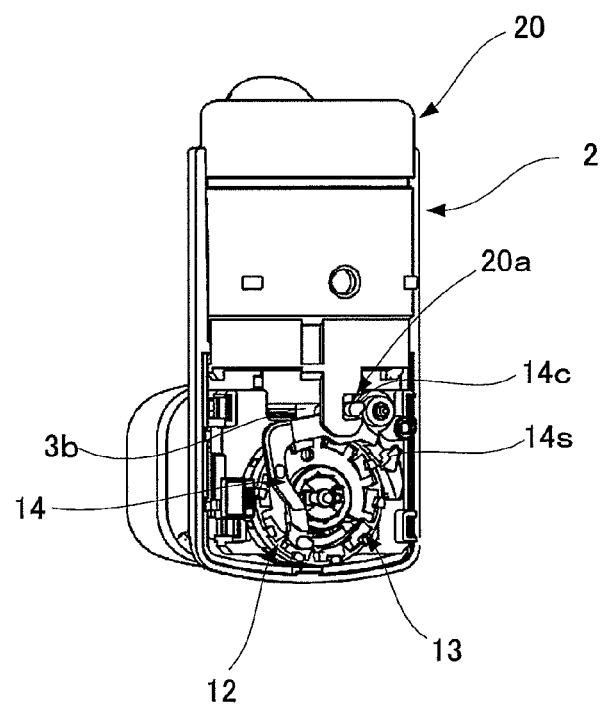
FIG. 43 is a perspective view showing an operational state following FIG. 42.
Figure 44:
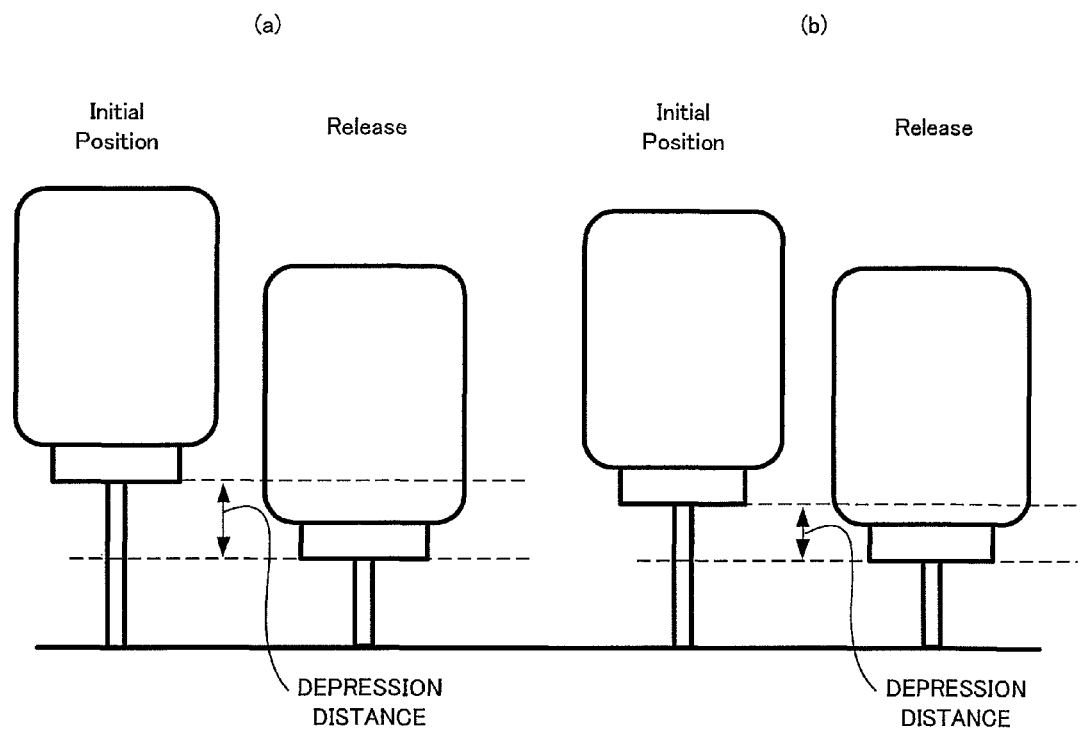
FIG. 44 is an explanatory diagram of an aerosol canister.
Figure 45:
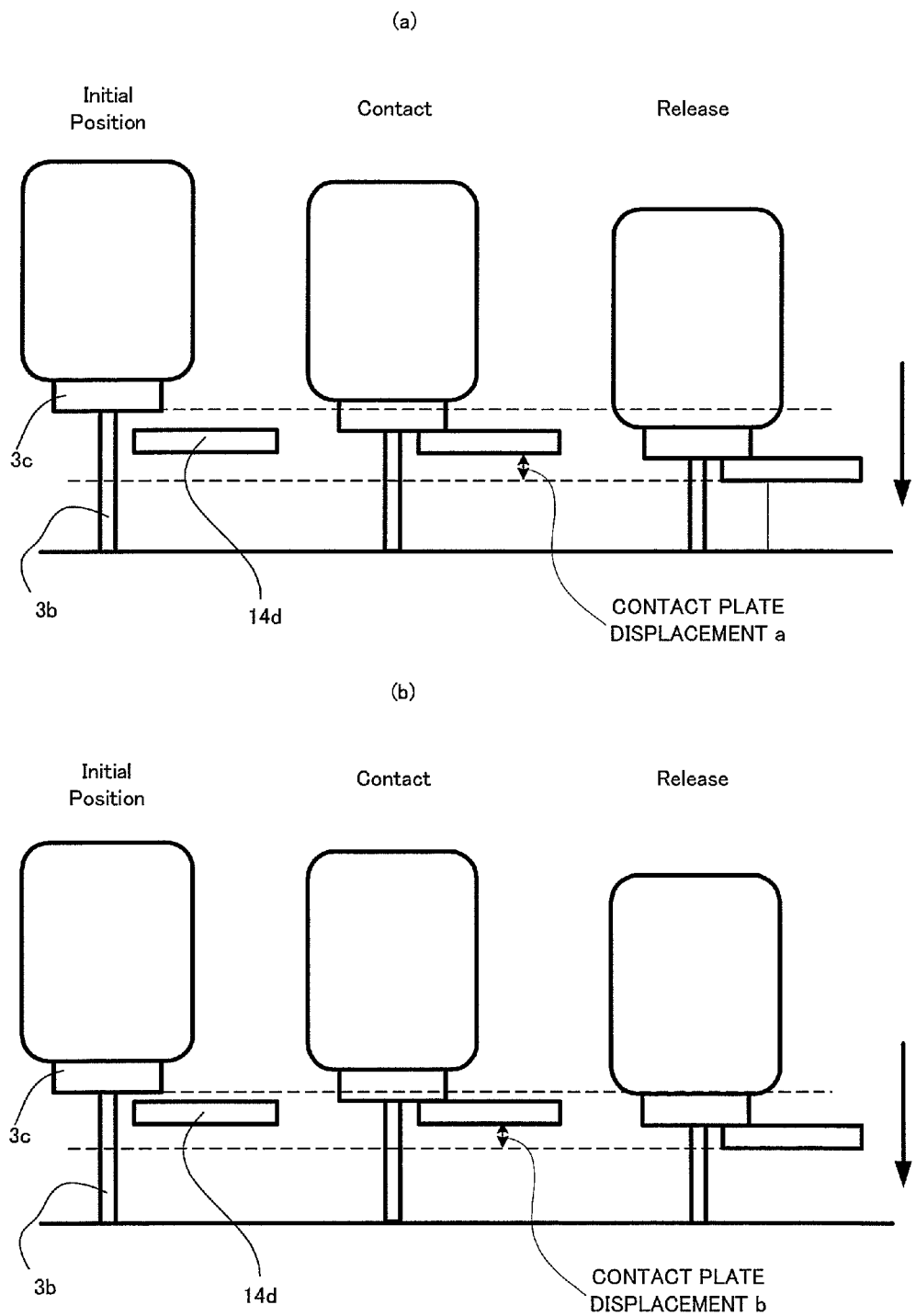
FIG. 45 is an explanatory diagram showing an operation of an aerosol canister and a contact plate.
Figure 46:
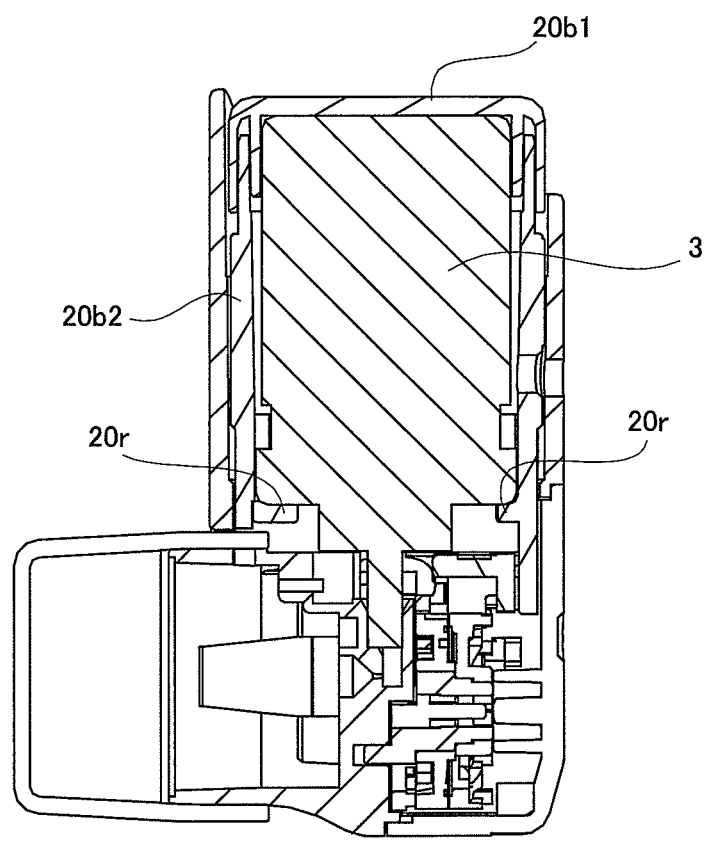
FIG. 46 is a cross sectional view showing another example of a metered dose inhaler.
Figure 47:
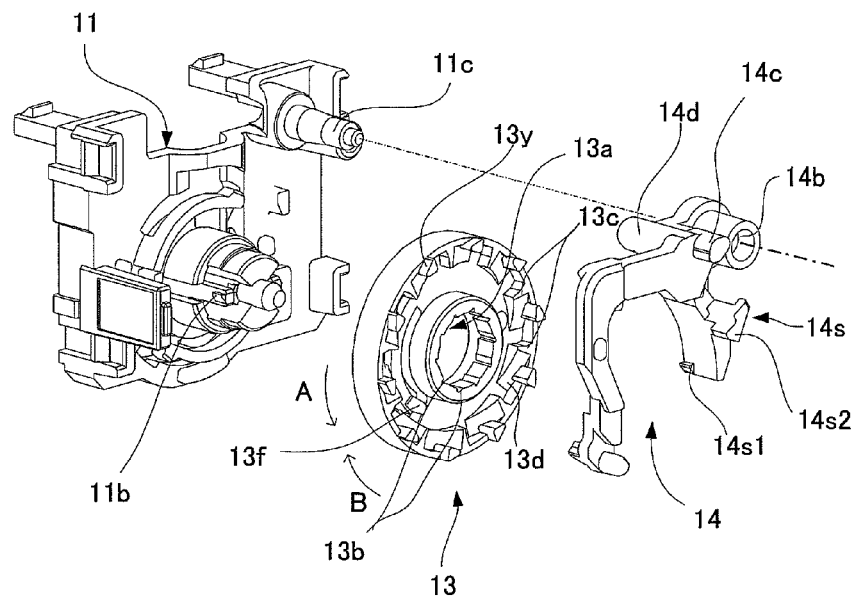
FIG. 47 is a perspective view exploding a display member and a control lever.
Figure 48:
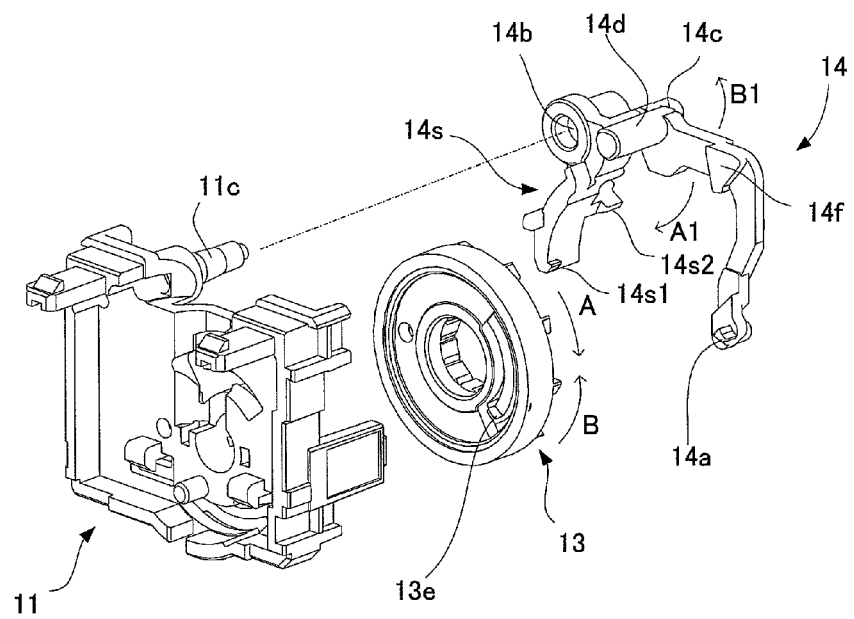
FIG. 48 is a perspective view exploding a display member and a control lever.
Figure 49:
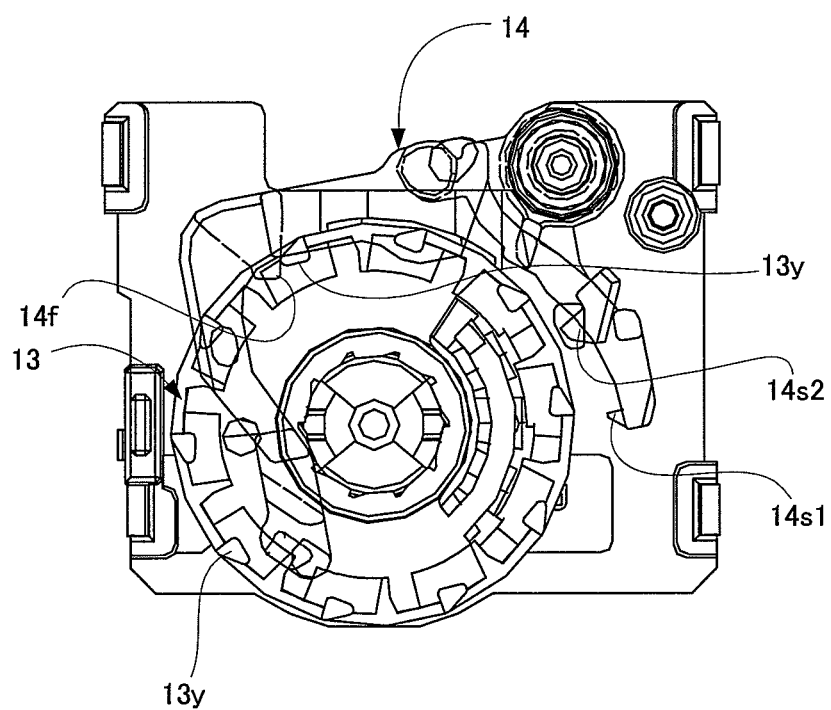
FIG. 49 is a front view showing an operation of the control lever shown in FIG. 47.

1 Metered dose inhaler
2 Housing body
2f Thin film portion
2g Through-hole
3 Aerosol canister
3a Canister body
3b Valve stem
4 Mouthpiece
5 Mouthpiece cap
5a Protrusion
10, 100 Dose counter
12 Display member
13 Display member
14, 140 Control lever
20, 200 Control cap
20a Junction member
20b, 200b Cap portion
101 Auxiliary spring
300 Lock member

The invention claimed is:

1. A metered dose inhaler comprising: an aerosol canister including a canister body, a valve stem extending from the canister body, and a spring urging the valve stem, the valve stem being depressed to release contents of the aerosol canister; a housing body, provided with a holder holding the valve stem of the aerosol canister, to house the aerosol canister; a dose counter including at least one display member rotatably supported inside the housing body, and a control lever supported inside the housing body to rotate the display member; and a control cap including at least one junction member capable of engaging the control lever, and a cap portion, formed as a shell surrounding the circumferential wall of the canister body so as to cover the canister body, and extending from an end of the canister body that is opposite to the valve stem and toward the valve stem, the aerosol canister being supported in the housing body to enable the canister body to be depressed against an urging force of the spring, the canister body of the aerosol canister including an engaging part to engage the control lever, the control lever being movable between a first position and a second position, the first position being a predetermined position between a tip of the valve stem and the engaging part, and the second position being a depressed position of the control lever engaging the engaging part of the canister body, the control cap co-operating with the canister body to be depressed from an initial position, and co-operating with the canister body to return to the initial position from a depressed position by the spring of the aerosol canister, the engaging part of the canister body engaging the control lever to move the control lever from the first position to the second position, when the canister body is depressed with the control cap, the junction member of the control cap engaging with the control lever so as to bias the control lever to move from the second position to the first position when returning to the initial position, and the control lever rotating the display member when moving from the first position to the second position, or when returning to the first position from the second position.

2. A metered dose inhaler according to claim 1, wherein the control lever engages the display member and rotates the display member when moving from the second position to the first position.

3. A metered dose inhaler according to claim 2,
wherein the control lever includes a stopper, which locks the display member at the first position, and unlocks the display member at the second position.

4. A metered dose inhaler according to claim 2,
wherein the control lever includes a protrusion capable of engaging the junction member, and is swingably supported between the first position and the second position,
wherein the control lever swings from the first position to the second position in response to depression of the control cap, and wherein the junction member and the protrusion move together without engaging each other following the swing of the control lever in response to depression of the control cap, and
wherein the junction member moves the control lever from the second position to the first position by being engaged by the protrusion, when moved with the control cap returning to the initial position.

5. A metered dose inhaler according to claim 2, wherein the canister body includes a step on a surface having the valve stem, and wherein the step comprises the engaging part.

6. A metered dose inhaler according to claim 1, further comprising:
a mouthpiece detachably attached to the housing body,
wherein contents of the aerosol canister are ejected out of the housing body through the mouthpiece.

7. A metered dose inhaler according to claim 1, wherein the dose counter further comprises an auxiliary spring to return the control lever.

* * * * *